(12) United States Patent
Hsu et al.

(10) Patent No.: US 7,101,487 B2
(45) Date of Patent: Sep. 5, 2006

(54) MAGNETORHEOLOGICAL FLUID COMPOSITIONS AND PROSTHETIC KNEES UTILIZING SAME

(75) Inventors: Henry Hsu, Aliso Viejo, CA (US); Charles R. Bisbee, III, Mission Viejo, CA (US); Michael Lars Palmer, Ladera Ranch, CA (US); Ronald J. Lukasiewicz, Carlsbad, CA (US); Michael W. Lindsay, Mission Viejo, CA (US); Stephen W. Prince, Mission Viejo, CA (US)

(73) Assignee: Ossur Engineering, Inc., Albion, MI (US)

( * ) Notice: Subject to any disclaimer, the term of this patent is extended or adjusted under 35 U.S.C. 154(b) by 68 days.

(21) Appl. No.: 10/722,313

(22) Filed: Nov. 25, 2003

(65) Prior Publication Data

US 2004/0217324 A1 Nov. 4, 2004

Related U.S. Application Data

(60) Provisional application No. 60/467,722, filed on May 2, 2003.

(51) Int. Cl.
*H01F 1/44* (2006.01)
(52) U.S. Cl. .................................. 252/62.52
(58) Field of Classification Search ............. 252/62.52; 623/24, 26, 39
See application file for complete search history.

(56) References Cited

U.S. PATENT DOCUMENTS

| | | | |
|---|---|---|---|
| 2,519,449 A | 8/1950 | Findley | |
| 2,804,955 A | 9/1957 | Gill, Jr. | |
| 3,177,998 A | 4/1965 | Rossez | |
| 3,360,475 A | 12/1967 | Rossez et al. | |
| 4,224,173 A | 9/1980 | Reick | |
| 4,284,518 A | 8/1981 | Reick | |
| 4,381,244 A | 4/1983 | Berkowitz et al. | |
| 4,687,596 A | 8/1987 | Borduz et al. | |
| 4,732,706 A | 3/1988 | Borduz et al. | |
| 4,790,522 A | 12/1988 | Drutchas, deceased | |
| 5,277,281 A | 1/1994 | Carlson et al. | |
| 5,354,488 A | 10/1994 | Shtarkman et al. | |
| 5,382,373 A * | 1/1995 | Carlson et al. ........... | 252/62.55 |
| 5,398,917 A | 3/1995 | Carlson et al. | |
| 5,449,313 A | 9/1995 | Kordonsky et al. | |
| 5,490,187 A | 2/1996 | VanSiclen et al. | |
| 5,505,880 A | 4/1996 | Kormann et al. | |

(Continued)

FOREIGN PATENT DOCUMENTS

EP 0 628 296 A2 5/1994

(Continued)

OTHER PUBLICATIONS

Carlson et al, "Smart Prosthetics Based on Magnetorheological Fluids", , 8th Annual Symposium on Smart Structures and Material, Mar. 2001.*

(Continued)

*Primary Examiner*—C. Melissa Koslow
(74) *Attorney, Agent, or Firm*—Knobbe, Martens, Olson & Bear, LLP

(57) ABSTRACT

The present invention relates in one embodiment to magnetorheological fluids utilized in prosthetic joints in general and, in particular, to magnetorheological fluids utilized in controllable braking systems for prosthetic knee joints. Preferred magnetorheological fluids of the present invention comprises polarizable iron particles, a carrier fluid, and optionally an additive. Preferred additives include, but are not limited to functionalized carrier fluids as well as derivatized fluoropolymers. Preferred carrier fluids include, but are not limited, to perfluorinated polyethers.

54 Claims, 8 Drawing Sheets

U.S. PATENT DOCUMENTS

| | | | |
|---|---|---|---|
| 5,518,639 A | 5/1996 | Luk et al. | |
| 5,525,249 A | 6/1996 | Kordonsky et al. | |
| 5,545,233 A | 8/1996 | Fitzlaff | |
| 5,547,049 A | 8/1996 | Weiss et al. | |
| 5,549,837 A | 8/1996 | Ginder et al. | |
| 5,571,205 A | 11/1996 | James | |
| 5,577,948 A | 11/1996 | Kordonsky et al. | |
| 5,578,238 A | 11/1996 | Weiss et al. | |
| 5,599,474 A | 2/1997 | Weiss et al. | |
| 5,629,092 A | 5/1997 | Gay et al. | |
| 5,645,752 A | 7/1997 | Weiss et al. | |
| 5,670,077 A | 9/1997 | Carlson et al. | |
| 5,683,615 A | 11/1997 | Munoz | |
| 5,705,085 A | 1/1998 | Munoz et al. | |
| 5,711,746 A | 1/1998 | Carlson | |
| 5,728,174 A | 3/1998 | Fitzlaff | |
| 5,816,372 A | 10/1998 | Carlson et al. | |
| 5,888,212 A | 3/1999 | Petrofsky et al. | |
| 5,893,891 A | 4/1999 | Zahedi | |
| 5,900,184 A | 5/1999 | Weiss et al. | |
| 5,906,767 A | 5/1999 | Karol et al. | |
| 5,947,238 A | 9/1999 | Jolly et al. | |
| 5,985,168 A | 11/1999 | Phule | |
| 5,989,447 A | 11/1999 | Podszun et al. | |
| 5,990,054 A | 11/1999 | Willis | |
| 6,027,664 A | 2/2000 | Weiss et al. | |
| 6,095,486 A | 8/2000 | Ivers et al. | |
| 6,149,832 A | 11/2000 | Foister | |
| 6,168,634 B1 | 1/2001 | Schmitz | |
| 6,186,290 B1 | 2/2001 | Carlson | |
| 6,203,717 B1 | 3/2001 | Munoz et al. | |
| 6,352,144 B1 | 3/2002 | Brooks | |
| 6,395,193 B1 | 5/2002 | Kintz et al. | |
| 6,423,098 B1 | 7/2002 | Biedermann | |
| 6,443,993 B1 | 9/2002 | Koniuk | |
| 6,475,404 B1 | 11/2002 | Carlson | |
| 6,503,414 B1 | 1/2003 | Kordonsky et al. | |
| 6,517,585 B1 | 2/2003 | Zahedi et al. | |
| 6,547,983 B1 | 4/2003 | Iyengar | |
| 6,547,986 B1 | 4/2003 | Kintz et al. | |
| 6,599,439 B1 | 7/2003 | Iyengar et al. | |
| 6,610,101 B1 | 8/2003 | Herr et al. | |
| 6,679,920 B1 | 1/2004 | Biedermann et al. | |
| 6,780,343 B1 * | 8/2004 | Hata et al. | 252/62.52 |
| 2001/0029400 A1 | 10/2001 | Deffenbaugh et al. | |
| 2002/0036127 A1 | 3/2002 | Carlson et al. | |
| 2002/0052663 A1 | 5/2002 | Herr et al. | |
| 2002/0130305 A1 | 9/2002 | Iyengar | |
| 2002/0138153 A1 | 9/2002 | Koniuk | |
| 2002/0171067 A1 | 11/2002 | Jolly et al. | |
| 2003/0006395 A1 | 1/2003 | Hata et al. | |
| 2003/0025102 A1 | 2/2003 | John et al. | |
| 2003/0047705 A1 | 3/2003 | Iyengar et al. | |
| 2003/0057395 A1 | 3/2003 | Iyengar et al. | |
| 2003/0071238 A1 | 4/2003 | Kintz et al. | |

FOREIGN PATENT DOCUMENTS

| | | | |
|---|---|---|---|
| EP | 0636 273 B1 | 8/1997 | |
| EP | 0801 403 A1 | 10/1997 | |
| EP | 1 125 825 A2 | 8/2001 | |
| GB | 2 244 006 A | 11/1991 | |
| GB | 2 264 348 A | 8/1993 | |
| GB | 2 268 070 A | 1/1994 | |
| GB | 2 328 160 A | 2/1999 | |
| GB | 2 334 891 A | 9/1999 | |
| WO | WO 94/10692 A | 5/1994 | |
| WO | WO 95/26171 | 10/1995 | |
| WO | WO 96/41599 | 12/1996 | |
| WO | WO 98/38951 | 9/1998 | |
| WO | WO 99/29272 | 6/1999 | |
| WO | WO 00/38599 | 7/2000 | |
| WO | WO 01/43668 A1 | 6/2001 | |
| WO | WO 01/84567 A2 | 11/2001 | |
| WO | WO 02/10281 | * | 2/2002 |
| WO | WO 02/45102 A1 | 6/2002 | |

OTHER PUBLICATIONS

*Dupont Krytox performance lubricants*, Technical Information, Product Information.

*Dupont™ Krytox® Performance Lubricants product Overview*, Copyright 2002.

*Dupont™ Krytox® Performance Lubricants*, www.exceed.dupont.com/krytox.

*Synthetic Lubricants and High-Performance Functional Fluids, Second Edition*, Perfluoroalkylpolyethers, Gregory A. Bell et al.

*DuPont Performance Lubricants Introduces New Line of Linear Krytox® Lubricants*, News Release, Feb. 24, 2003.

*Uniflor, 8100 Series, 8500 Series, 8700 Series, 8900 Series*, Product Descriptions and Properties, www.nyeuniflor.com; www.nyelubricants.com/datasheets.

*Fomblin PFPE: Additives*, Solvay Solexis, Product Data Sheet, www.solvaysolexis.com.

*Carbonyl Iron Powders*, International Specialty Products.

*BASF Product Information*, BASF, Carbonyl Iron Powder data sheets.

*Properties and Applications of Commercial Magnetorheological Fluids*, Mark R. Jolly et al., Thomas Lord Research Center.

*Commercial Magneto-Rheological Fluid Devices*, D. Carlson et al., Lord Corporation.

*What Makes a Good Mr. Fluid?*, J. David Carlson, Presented at the 8th Internatioal Conference on Electroheological (ER) Fluids and Magneto-rheological (MR) Suspensions, Nice, Jul. 9-13, 2001.

*Smart Prosthetics Based on Magnetorheological Fluids*, J. David Carlson et al., 8th Annual Symposium on Smart Structures and Materials, Newport Beach, CA Mar. 2001.

*State-of-the-Art Prosthetic Leg Incorporates Magneto-Rheological Technology*, 42 Medical Product Manufacturing News, devicelink.com, Nov. 2000.

*C-Leg, A new dimension in amputee mobility*, Otto Bock, Data Sheet 1997.

* cited by examiner

MAGNETORHEOLOGICAL FLUID COMPOSITIONS AND PROSTHETIC KNEES UTILIZING SAME

RELATED APPLICATIONS DATA

This application claims priority under 35 U.S.C. 119(e) from provisional application Ser. No. 60/467,722 filed May 2, 2003, the entirety of which is hereby incorporated by reference.

BACKGROUND OF THE INVENTION

1. Field of the Invention

The present invention relates in one embodiment to magnetorheological fluids utilized in prosthetic joints in general and, in particular, to magnetorheological fluids utilized in controllable braking systems for prosthetic knee joints.

2. Description of the Related Art

Three types of variable-torque brakes have been employed in prosthetic knees in the past: (i) dry friction brakes where one material surface rubs against another surface with variable force; (ii) viscous torque brakes using hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Each of these technologies, as conventionally practiced in the field of prosthetics, can pose certain disadvantages.

Though dry friction brakes can generally provide a substantial torque range for their size, undesirably, they are often difficult to control. After extended use, the frictional pads tend to wear, thereby changing the frictional characteristics of the brake and the torque response for a given commanded torque. Disadvantageously, this can cause unreliable damping performance, and hence adversely affect the gait of the amputee and also cause discomfort to the amputee. Consequently, dry friction brakes may need frequent servicing and/or replacement which undesirably adds to the cost.

Under high loading conditions, viscous torque brakes are susceptible to leakage of hydraulic fluid and possibly other damage due to excessive pressure build-up. Disadvantageously, this can result in an irreversible state, since once the brake unit is overloaded it cannot return to normal. Therefore, such a viscous torque brake for a prosthetic joint is prone to catastrophic failure, and hence can be unreliable and detrimental to the safety of an amputee.

In certain MR brakes and dampers, the interaction of the MR fluid with the device causes increased pressure, seal deterioration, or a combination of the two. Another possible cause of these adverse effects is decomposition of the MR fluid. Once the seals fail or the MR fluid decomposes, the prosthetic knee is no longer suitable for use.

SUMMARY OF THE INVENTION

In accordance with preferred embodiments, there is provided a magnetorheological fluid (MR fluid) comprising polarizable particles, a carrier fluid, and optionally an additive. In one embodiment, the polarizable particles comprise iron particles ranging in size from about 0.1 to about 100 microns, preferably from about 0.2 to about 50 microns, from about 0.4 to about 10 microns, or from about 0.5 to about 9 microns, but also including about 0.3, 0.6, 0.7, 0.8, 0.9, 1, 2, 3, 4, 5, 6, 7, 8, 11, 12, 13, 14, 15, 16, 17, 18, 19, 20, 25, 30, 40, 60, 70, 80, and 90 microns, and ranges encompassing such sizes. In certain embodiments, iron particles comprise from about 1 to about 60% (v/v) of the total MR fluid volume, preferably from about 10 to about 50% (v/v), from about 20 to about 40% (v/v), but also including about 5, 15, 25, 30, 35, 45, and 55% (v/v) and ranges encompassing such percentages.

Suitable candidates for carrier fluids include, but are not limited to, silicone, hydrocarbon, esters, ethers, fluorinated esters, fluorinated ethers, mineral oil, unsaturated hydrocarbons, and water based fluids. In one embodiment, a preferred carrier fluid comprises an aliphatic hydrocarbon. In another embodiment, a preferred carrier fluid comprises a perfluorinated polyether ("PFPE").

In one embodiment, a preferred additive comprises a functionalized fluoropolymer, including, but not limited to, a parafluoropropene and oxygen polymerized amide derivative. In another embodiment, a preferred additive comprises a functionalized carrier fluid. Suitable candidates for monofunctionalized PFPE carrier fluid derivatives include, but are not limited to silane, phosphate, hydroxyl, carboxylic acid, alcohol and amine functions. Suitable candidates for difunctional PFPE carrier fluid derivatives include, but are not limited to, dihydroxyl, ethoxy ether, isocyanate, aromatic, ester and alcohol functions. In one embodiment, a preferred functionalized PFPE carrier fluid comprises a poly(hexafluoropropylene epoxide) with a carboxylic acid located on the terminal fluoromethylene group. In one embodiment, the additive comprises from about 0.1 to about 20% (v/v) of the carrier fluid, preferably from about 1 to about 15% (v/v), or from about 2 to about 10% (v/v), but also including about 2.5, 3, 3.5, 4, 4.5, 5, 5.5, 6, 6.5, 7, 7.5, 8, 8.5, 9, 9.5, 11, 12, 13, 14, 16, 17, 18, and 19% (v/v) and ranges encompassing such percentages.

In one embodiment, a preferred MR fluid comprises about 28% (v/v) particles, and about 72% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid comprises about 32% (v/v) particles, and about 68% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid comprises about 28% (v/v) particles and about 72% (v/v) fluid component wherein said fluid component comprises about 5% (v/v) parafluoropropene and oxygen polymerized amide derivative additive and about 95% (v/v) PFPE oil carrier fluid. In another embodiment, a preferred MR fluid comprises about 32% (v/v) particles and about 68% (v/v) fluid component wherein said fluid component comprises about 5% (v/v) parafluoropropene and oxygen polymerized amide derivative additive and about 95% (v/v) PFPE oil carrier fluid. In embodiments containing PFPE oil, the PFPE oil may comprise substantially all one PFPE oil or a mixture of one or more PFPE oils.

In one embodiment, an MR fluid is specifically designed for use in a shear mode device. For such a device, mechanically hard particles are desired. The carrier fluid also desirably experiences a less dramatic viscosity change over temperature changes as compared to other fluids. This may be measured in terms of a viscosity index (test method ASTM D-2270) with preferred carrier fluids having higher viscosity indices. In one embodiment, preferred carrier fluids have viscosity indices preferably ranging from about 100 to about 340 based on kinematic viscosity at 104 and 212° F., from about 120 to about 320, from about 140 to about 300, but also including 160, 180, 200, 220, 240, 255, 260, 280, and ranges encompassing these amounts. One embodiment that accomplishes this includes a carrier fluid comprising one or more PFPE oils. For example, a preferred PFPE fluid, UNIFLOR™ 8510 has a viscosity index of 255. Without wishing to be bound by any theory, it is believed that preferred PFPE oils of certain embodiments demonstrate desirable viscosity indices due to their narrow distribution of molecular weights. Also, the MR fluid desirably does not produce a significant amount of vapor in a sealed chamber so as to interfere with the function of the device. In one embodiment, a fluid component comprising PFPE oil carrier fluid and a functionalized fluoropolymer additive provides this property. Without wishing to be bound by any theory, it is believed that preferred PFPE oils of certain embodiments are less volatile, i.e. lower vapor pressures than other oils, because they have much higher molecular weights, e.g. about 2,000 to about 15,000, and therefore do not produce a significant amount of vapor.

In addition, a shear mode device should provide sufficient torque, for example torque production in one embodiment may be about 0.1 to about 200 Newton-meters, more preferably about 0.3 to about 150 Newton-meters, even more preferably about 0.5 to about 100 Newton-meters, but also including about 0.8, 1, 2, 3, 4, 5, 6, 7, 8, 9, 10, 20, 30, 40, 50, and 75 Newton-meters. In one embodiment, maintaining a sufficient ratio of particles, such as iron particles, to MR fluid provides for this. In one embodiment, a suitable ratio is achieved when the iron particles comprise from about 1 to about 60% (v/v) of the total MR fluid volume, preferably from about 10 to about 50% (v/v), more preferably from about 20 to about 40% (v/v), but also including about 5, 15, 25, 30, 35, 45, and 55% (v/v) and ranges encompassing these percentages.

In accordance with preferred embodiments, there is provided a MR fluid comprising polarizable particles, a carrier fluid, and optionally an additive for use in a prosthetic knee, for example, a knee as described in U.S. Patent Publication 2001/0029400A1. In one embodiment, the prosthetic knee comprises at least two adjacent surfaces adapted for shear movement relative to one another wherein the MR fluid is contained between said adjacent surfaces. In one embodiment, the MR fluid used in combination with the knee comprises PFPE oil carrier fluid and particles, such as polarizable particles described above. In one embodiment, the polarizable particles comprise iron particles ranging in size from about 0.1 to about 100 microns, preferably from about 0.2 to about 50 microns, more preferably from about 0.4 to about 10 microns, even more preferably from about 0.5 to about 9 microns, but also including about 0.3, 0.6, 0.7, 0.8, 0.9, 1, 2, 3, 4, 5, 6, 7, 8, 11, 12, 13, 14, 15, 16, 17, 18, 19, 20, 25, 30, 40, 60, 70, 80, and 90 microns, and ranges encompassing these sizes. In certain embodiments, iron particles comprise from about 1 to about 60% (v/v) of the total MR fluid volume, preferably from about 10 to about 50% (v/v), more preferably from about 20 to about 40% (v/v), but also including about 5, 15, 25, 30, 35, 45, and 55% (v/v) and ranges encompassing such percentages.

In another embodiment, the MR fluid used in combination with a prosthetic knee optionally includes an additive. In one embodiment, a preferred additive comprises a functionalized fluoropolymer, more preferably a parafluoropropene and oxygen polymerized amide derivative. In another embodiment, a preferred additive comprises a functionalized carrier fluid. Suitable candidates for monofunctionalized PFPE carrier fluid derivatives include, but are not limited to silane, phosphate, hydroxyl, carboxylic acid, alcohol and amine functions. Suitable candidates for difunctional PFPE carrier fluid derivatives include, but are not limited to, dihydroxyl, ethoxy ether, isocyanate, aromatic, ester and alcohol functions. In one embodiment, a preferred functionalized PFPE oil comprises a poly(hexafluoropropylene epoxide) with a carboxylic acid located on the terminal fluoromethylene group. In one embodiment, the additive comprises from about 0.1 to about 20% (v/v) of the carrier fluid, preferably from about 1 to about 15% (v/v), more preferably from about 2 to about 10% (v/v), but also including about 2.5, 3, 3.5, 4, 4.5, 5, 5.5, 6, 6.5, 7, 7.5, 8, 8.5, 9, 9.5, 11, 12, 13, 14, 16, 17, 18, and 19% (v/v), and ranges encompassing these amounts.

In another embodiment, the passage or cavity of the knee that holds the MR fluid contains a volume of about 1 to about 10 ml, preferably from about 2 to about 9 ml, more preferably from about 3 to about 8 ml, but also including about 4, 5, 6, and 7 ml, and ranges encompassing these volumes. In one embodiment, the MR fluid fills the cavity to about 70% of its capacity, but ranges from about 50 to about 100% as well about 55, 60, 65, 75, 80, 85, 90 and 90% and ranges encompassing these amounts are also acceptable.

In another embodiment, the MR fluid used in combination with a prosthetic knee in shear mode in one embodiment utilizes a MR fluid that is operable over a temperature range from about 10 to about 115° F., but also including about 20, 30, 40, 50, 60, 70, 80, 90, 100, and 110° F. Operability in one embodiment depends on viscosity, wherein the carrier fluid desirably has a viscosity at 104° F. of about 10 to about 100 cSt (centistokes), more preferably about 30 to about 80 cSt, even more preferably about 50 to about 70 cSt, but also including about 10, 20, 25, 35, 40, 45, 55, 60, 65, 75, 85, 90, and 95 cSt.

Desirably, operation of a prosthetic knee in shear mode in one embodiment preferably utilizes a carrier fluid with a pour point preferably ranging from about −70° C. to about −40° C., from about −65° C. to about −45° C., but also including about −50° C., −55° C., and −60° C., and ranges encompassing these temperatures. In another embodiment, operation of a prosthetic knee in shear mode preferably utilizes a carrier fluid with a percent volatility at 121° C. preferably ranging from about 0.01% to about 20%, from about 0.02% to about 15%, from 0.03% to about 12%, but also including about 0.05%, 0.08%, 0.1%, 0.2%, 0.3%, 0.4%, 0.5%, 0.7%, 0.9%, 1%, 3%, 5%, 7%, 9%, 17%, and ranges encompassing these percentages.

In one embodiment, a preferred MR fluid used in combination with a prosthetic knee in shear mode comprises about 28% (v/v) particles, and about 72% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid used in combination with a prosthetic knee in shear mode comprises about 32% (v/v) particles, and about 68% (v/v) fluid component wherein said fluid component. comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid used in combination with a prosthetic knee in shear mode comprises about 28% (v/v) particles, and about 72% (v/v) fluid component wherein said fluid component comprises about 5% (v/v) parafluoropropene and oxygen polymerized amide derivative additive and about 95% (v/v) PFPE oil carrier fluid. In another embodiment, a preferred MR fluid comprises about 32% (v/v) particles and about 68% (v/v) fluid component wherein said fluid component comprises about 5% (v/v) parafluoropropene and oxygen polymerized amide derivative additive and about 95% (v/v) PFPE oil carrier fluid. In embodiments containing PFPE oil, the PFPE oil may comprise substantially all one PFPE oil or a mixture of one or more PFPE oils.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular. preferred embodiment(s) disclosed.

BRIEF DESCRIPTION OF THE DRAWINGS

FIGS. 1 and 2 correspond to FIGS. 4 and 5, respectively, of U.S. Patent Publication 2001/0029400A1 (application Ser. No. 09/767,367), filed Jan. 22, 2001, entitled "ELECTRONICALLY CONTROLLED PROSTHETIC KNEE," the entire disclosure of which is hereby incorporated by reference herein. More specifically, the description of the drawings and the item numbers depicted in the drawings are described in detail in the above referenced patent publication. FIG. 1 is a detailed exploded perspective view of a magnetorheologically actuated prosthetic knee having features and advantages in accordance with one preferred embodiment of the present invention. FIG. 2 is a cross section view of the prosthetic knee of FIG. 1.

DETAILED DESCRIPTION OF THE PREFERRED EMBODIMENTS

Figure 1:
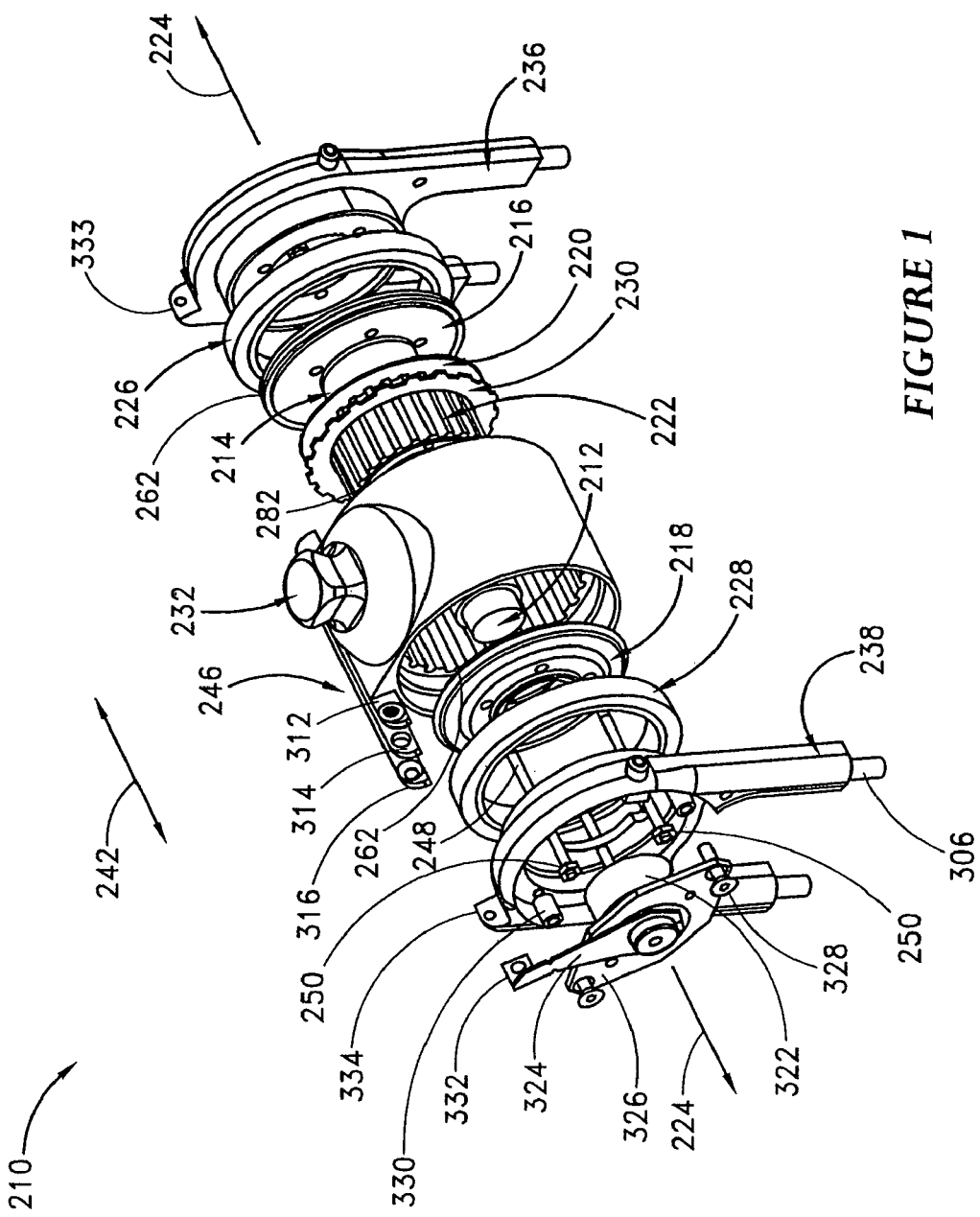
FIGS. 1 and 2 depict one embodiment of a prosthetic knee suitable for use in preferred embodiments.
Figure 2:
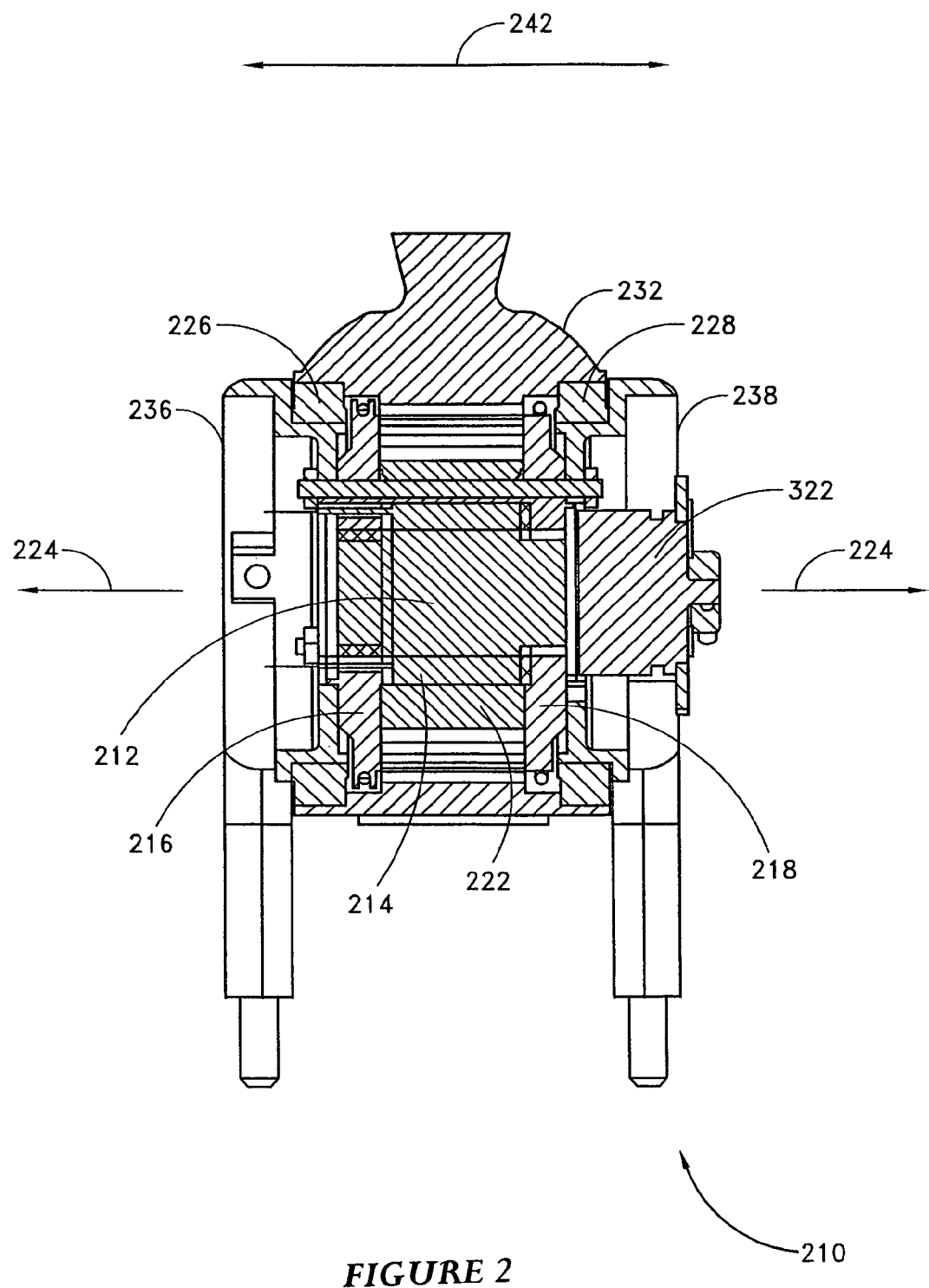

Disclosed herein are magnetorheological fluids (MR fluids) suitable for use in magnetorheological knee brakes or actuators. More particularly, the disclosed MR fluids may be applicable to prosthetic knee joints which operate in shear mode, for example, where the MR fluid is provided between adjacent surfaces, such as between parallel plates or in the annular space between inner and outer cylinders. Certain embodiments of a magnetorheological knee brake or actuator that may employ the MR fluids as described herein are described in U.S. Patent Publication 2001/0029400A1 (application Ser. No. 09/767,367), filed Jan. 22, 2001, entitled "ELECTRONICALLY CONTROLLED PROSTHETIC KNEE," the entire disclosure of which is hereby incorporated by reference herein. FIGS. 1 and 2, corresponding to FIGS. 4 and 5 of U.S. Patent Publication 2001/0029400A1, also depict one embodiment of a magnetorheological knee brake or actuator that may employ the MR fluids as described herein. Certain embodiments of a control scheme and system for magnetorheological knee brakes or actuators are described in copending U.S. Patent Publication 2002/0052663A1 (application Ser. No. 09/823,931), filed Mar. 29, 2001, entitled "SPEED-ADAPTIVE AND PATIENT-ADAPTIVE PROSTHETIC KNEE," the entire disclosure of which is hereby incorporated by reference herein. It will be appreciated, however, that the MR fluids as described herein may have applicability to other devices which utilize MR fluids, including but not limited to, other devices operating in a shear mode.

In one embodiment, the magnetorheological fluid preferably comprises a plurality of iron, ferrous or magnetic particles suspended in fluid. These suspended particles form torque producing chains in response to an applied magnetic field. Thus, the magnetorheological (MR) fluid undergoes a rheology or viscosity change or variation, which is dependent on the magnitude of the applied magnetic field. In turn, this variation in the bulk fluid viscosity determines the magnitude of the shearing force/stress or torque generated, and hence the level of damping or braking provided by the prosthetic knee or other device. Typically, the bulk viscosity of the MR fluid increases with increasing strength of the applied field. By controlling the magnitude of this magnetic field, the rotary motion of an artificial limb is rapidly and precisely adjusted and/or controlled, for example, to control the flexion and extension during swing and stance phases to provide a more natural and safe ambulation for the amputee. Preferably the MR fluid has one or more of the following properties: a high magnetic flux capacity and low magnetic remanence and low viscosity while having a large magnetic field induced shearing stress so that, advantageously, a prosthetic knee in one embodiment, provides a wide dynamic torque range.

In one embodiment, the MR fluid preferably comprises a carrier fluid with polarizable ferrous or iron particles. As used herein, the term carrier fluid is a broad term used in its ordinary sense and includes embodiments wherein the specific carrier fluids described below are the primary component and embodiments wherein the carrier fluid comprises these specific fluids as well as additives described below. In addition, embodiments wherein the additives described below are the primary carrier fluid are also contemplated. In one embodiment, such as when used between rotor-stator surfaces of U.S. 2001/0029400A1, these particles have a size on the order of a micron or a few microns. Ideally the MR fluid exhibits shear rate thinning behavior where MR fluid viscosity decreases with increasing shear rate. This advantageously minimizes the viscous torque due to shearing of the MR fluid between each rotor-stator pair under zero-field conditions (that is, when the electromagnet is not energized), and hence allows for a larger operating torque range. Further, in one embodiment MR fluids used in combination with a prosthetic knee desirably exhibit low off-state viscosity and therefore low off-state torque as torque is proportional to MR fluid viscosity. The viscosity of preferred MR fluids in certain embodiments may be altered by one or more of the following: increasing or decreasing the particle loading, including an additive, changing the carrier fluid, or mixing two or more carrier fluids.

Suitable candidates for carrier fluids include, but are not limited to, silicone, hydrocarbon, esters, ethers, fluorinated esters, fluorinated ethers, mineral oil unsaturated hydrocarbons, and water based fluids. In one embodiment, the carrier fluid comprises substantially all one fluid. In another embodiment, the carrier fluid is a mixture of one or more carrier fluids. In one embodiment, the carrier fluid preferably comprises an aliphatic hydrocarbon. In another embodiment the carrier fluid preferably comprises a perfluorinated polyether (PFPE), also known as perfluoropolyether, perfluoroalkylether or perfluoropolyalkylether, fluid. In certain embodiments, a preferred PFPE oil comprises fluorine end capped branched homopolymers of hexafluoropropylene epoxide with the following chemical structure:

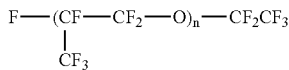

Where n=10–60

In another embodiment, a preferred PFPE oil comprises a branched PFPE containing pendent trifluoromethyl groups, (—$CF_3$), with the following structure:

Where n=5–65

In another embodiment, a preferred PFPE oil comprises a linear PFPE with the following structure:

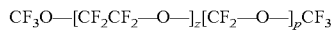

Where the ratio of z:p is between about 0.5:1 and 2:1, and z+p is between about 40 and about 180. In another embodiment, a preferred PFPE oil comprises a linear PFPE with the following structure:

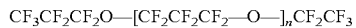

Where n=10–50

In another embodiment, a preferred PFPE oil comprises perfluoropropylpolyether. As presently contemplated preferred perfluorinated polyethers may be purchased from Nye Lubricants (Fairhaven, Mass., USA) and include, but are not limited to, UNIFLOR™ 8510, UNIFLOR™ 8130, UNIFLOR™ 8140, UNIFLOR™ 8730 and UNIFLOR™ 8970. Suitable perfluorinated polyethers may also be purchased from E.I. du Pont de Nemours and Company, (Wilmington, Del., USA) and include, but are not limited to, Krytox® GPL-103, Krytox® L-65 oil, Krytox® XP 1A4 oil, Krytox® L-100, Krytox® 1525, Krytox® 1525S, and Krytox® 1531.

Other ingredients can be optionally added to the carrier fluids of preferred embodiments to enhance the performance properties of preferred carrier fluids. In some embodiments, preferred additives include, but are not limited to, functionalized carrier fluids. In embodiments comprising perfluorinated polyethers, desirable additives can also include, but are not limited to, functionalized PFPE oils as well as derivatized fluoropolymers. Suitable candidates for monofunctionalized PFPE derivatives include, but are not limited to silane, phosphate, hydroxyl, carboxylic acid, alcohol and amine functions. Suitable candidates for difunctional PFPE derivatives include, but are not limited to, dihydioxyl, ethoxy ether, isocyanate, aromatic, ester and alcohol functions. More specifically, in one embodiment comprising perfluorinated polyethers, a preferred functionalized PFPE oil comprises a poly(hexafluoropropylene epoxide) with a carboxylic acid located on the terminal fluoromethylene group. As presently contemplated preferred functionalized PFPE oils are Krytox® 157 FSL and Krytox® 157 FSM available from E.I. du Pont de Nemours and Company, (Wilmington, Del., USA). In another embodiment, a preferred fluoropolymer comprises a parafluoropropene and oxygen polymerized amide derivative. As presently contemplated a preferred parafluoropropene and oxygen polymerized amide derivative additive is FOMBLIN DA 306 available from Solvay Solexis (Thorofare, N.J., USA).

Suitable candidates for polarizable ferrous or iron particles include, but are not limited to, particles ranging in size from about 0.1 to about 100 microns, preferably from about 0.2 to about 50 microns, more preferably from about 0.4 to about 10 microns, even more preferably from about 0.5 to about 9 microns, but also including about 0.3, 0.6, 0.7, 0.8, 0.9, 1, 2, 3, 4, 5, 6, 7, 8, 11, 12, 13, 14, 15, 16, 17, 18, 19, 20, 25, 30, 40, 60, 70, 80, and 90 microns, and ranges encompassing these sizes. In certain embodiments, preferred particles are mechanically hard. As presently contemplated preferred iron particles are available from BASF AG (Ludwigshafen, Germany) and include, but are not limited to, BASF Carbonyl Iron Powder OM, BASF Carbonyl Iron Powder HQ, BASF Carbonyl Iron Powder HS, BASF Carbonyl Iron Powder EW, BASF Carbonyl Iron Powder HS-I, and BASF Carbonyl Iron Powder HL-1. Other suitable iron particles may also be purchased from ISP Corporation (Wayne, N.J., USA). Other suitable ferrous or iron particles well known to those of skill in the art may also be used. In related embodiments, particles comprising magnetic or ferromagnetic materials other than iron may be used alone or in combination with iron-based particles.

In accordance with a preferred embodiment, the MR fluid composition comprises polarizable iron particles, PFPE carrier fluid, and an additive. In one embodiment, the iron particles comprise from about 1 to about 60% (v/v) of the total MR fluid volume, preferably from about 10 to about 50% (v/v), more preferably from about 20 to about 40% (v/v), but also including about 5, 15, 25, 30, 35, 45, and 55% (v/v) and ranges encompassing such percentages. To determine the weight of particles required to achieve the proper % (v/v), the required volume is multiplied by the density of the particles. In one embodiment, the additive comprises from about 0.1 to about 20% (v/v) of the carrier fluid, preferably from about 1 to about 15% (v/v), more preferably from about 2 to about 10% (v/v), but also including about 2.5, 3, 3.5, 4, 4.5, 5, 5.5, 6, 6.5, 7, 7.5, 8, 8.5, 9, 9.5, 11, 12, 13, 14, 16, 17, 18, and 19% (v/v) and ranges encompassing such percentages. For example, in one embodiment a preferred MR fluid comprises about 28% (v/v) iron particles and about 72% (v/v) fluid component wherein said fluid component comprises about 5% (v/v) a parafluoropropene and oxygen polymerized amide derivative additive and about 95% (v/v) PFPE carrier fluid. In another embodiment, a preferred MR fluid comprises about 32% (v/v) particles and about 68% (v/v) fluid component wherein said fluid component comprises about 5% (v/v) parafluoropropene and oxygen polymerized amide derivative additive and about 95% (v/v) PFPE oil carrier fluid. In another embodiment, a preferred MR fluid comprises about 28% (v/v) particles, and about 72% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid comprises about 32% (v/v) particles, and about 68% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In embodiments containing PFPE oil, the PFPE oil may comprise substantially all one PFPE oil or a mixture of one or more PFPE oils.

The MR fluid ingredients may be combined in any order and mixed by any suitable means including, but not limited to, stirring, agitation, sonification or blending. In accordance with a preferred embodiment, additives are first mixed with carrier fluids and stirred. Carrier fluid is added to the iron particles and the ingredients are stirred. The particles are then dispersed using sonification. The resulting MR fluid is then heated. A detailed example is provided below in the example section.

Figure 4:
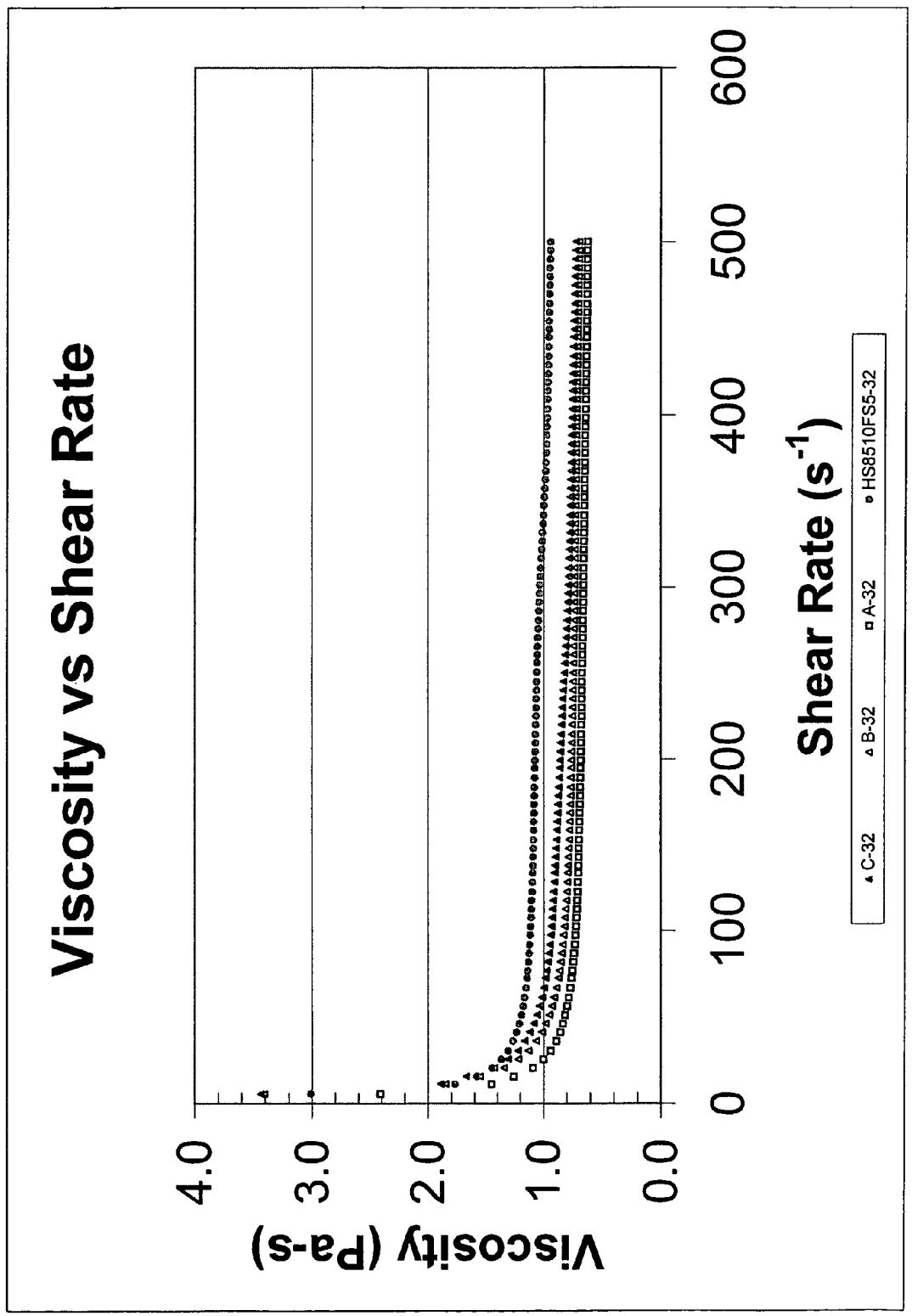
Figure 5:
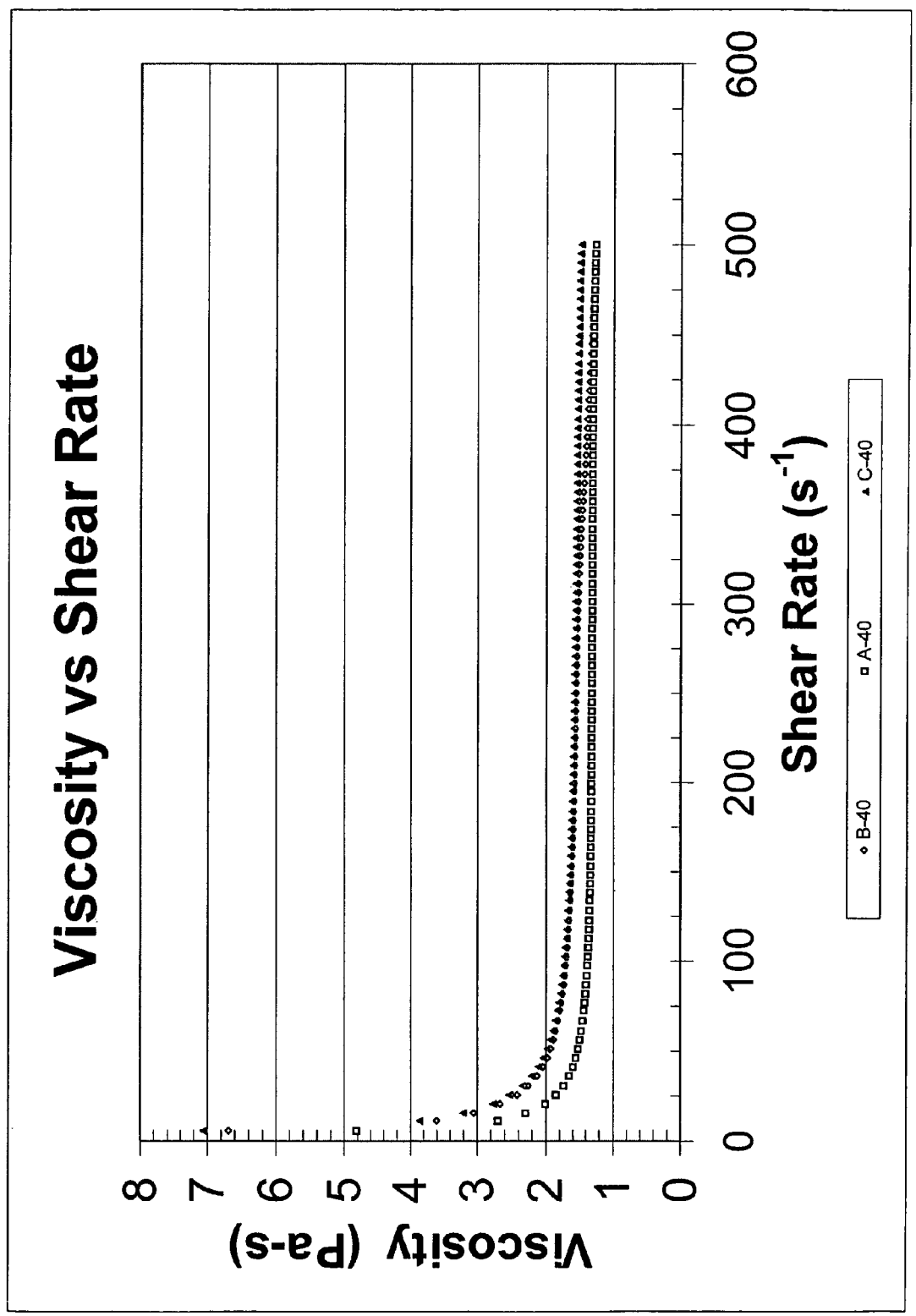

When the MR fluids as described herein are used in combination with a prosthetic knee, for example, a knee as described in U.S. Patent Publication 2001/0029400A1, certain characteristics of the fluid as well as the knee may be desired. In one embodiment, such as shown in FIGS. 4 and 5 of U.S. 2001/0029400A1, a knee may contain a cavity or passage for holding MR fluid between a plurality of rotors and stators. The number of rotors and stators in certain embodiments may be increased or reduced in order to alter the off-state or low-end torque properties of the MR fluid used in combination with the knee. In one embodiment, the number of rotors and stators preferably range from about 50 to about 90, preferably from about 55 to about 70, but also including about 57, 59, 61, 63, 65, 67, and ranges encompassing these amounts. The knee cavity may contain a volume of about 1 to about 10 ml, preferably from about 2 to about 9 ml, more preferably from about 3 to about 8 ml, but also including about 4, 5, 6, and 7 ml. In one embodiment, the MR fluid fills the cavity to about 70% of its total volume, but may range from about 50 to about 100% as well about 55, 60, 65, 75, 80, 85, 90 and 90%. The MR fluid advantageously demonstrates one or more of the following: relatively low volatility, stable viscosity, thermal stability, and a stable composition. In addition, in certain embodiments it is desirable that the cavity or passage containing the MR fluid does not exhibit undesirable pressure levels. Without wishing to be bound by any theory, it is believed that an unsuitable fluid may release gases or volatilize causing pressure within the prosthetic knee to increase to an undesirable level. If the pressure is too high, the integrity of the prosthetic knee seals can be compromised. In certain embodiments it is desirable that a prosthetic knee utilizing a MR fluid produces torque of about 0.1 to about 200 Newton-meters, more preferably about 0.3 to about 150 Newton-meters, even more preferably about 0.5 to about 100 Newton-meters, but also including about 0.8, 1, 2, 3, 4, 5, 6, 7, 8, 9, 10, 20, 30, 40, 50, and 75 Newton-meters.

Desirably, operation of a prosthetic knee in shear mode in one embodiment utilizes a MR fluid that is operable over a temperature range from about 10 to about 115° F., but also including about 20, 30, 40, 50, 60, 70, 80, 90, 100, and 110° F. Operability in one embodiment depends on viscosity, wherein the carrier fluid desirably has a viscosity at 104° F/ (40° C.) of about 10 to about 100 cSt, more preferably viscosity of about 30 to about 80 cSt, even more preferably viscosity of about 50 to about 70 cSt, but also including about 10, 20, 25, 35, 40, 45, 55, 60, 65, 75, 85, 90, and 95 cSt. The viscosity of preferred MR fluids in certain embodiments may be altered by one or more of the following: increasing or decreasing the particle loading, including an additive, changing the carrier oil, or mixing two or more carrier oils.

In one embodiment, an MR fluid is specifically designed for use in a shear mode device. For such a device, mechanically hard particles are desired. The carrier fluid also desirably experiences a less dramatic viscosity change over temperature changes as compared to other fluids. This may be measured in terms of a viscosity indices (test method ASTM D-2270) with preferred carrier fluids having higher viscosity indices. In one embodiment, preferred carrier fluids have viscosity indices preferably ranging from about 100 to about 340 based on kinematic viscosity at 104 and 212° F., from about 120 to about 320, from about 140 to about 300, but also including 160, 180, 200, 220, 240, 255, 260, 280, and ranges encompassing these amounts. One embodiment that accomplishes this includes a carrier fluid comprising one or more PFPE oils. For example, a preferred PFPE fluid, UNIFLOR™ 8510 has a viscosity index of 255. Without wishing to be bound by any theory, it is believed that preferred PFPE oils of certain embodiments demonstrate desirable viscosity indices due to their narrow distribution of molecular weights. Also, the MR fluid desirably does not produce a significant amount of vapor in a sealed chamber so as to interfere with the function of the device. In one embodiment, a fluid component comprising PFPE oil carrier fluid and a fluoropolymer additive provides this property. Without wishing to be bound by any theory, it is believed that preferred PFPE oils of certain embodiments are less volatile, i.e. lower vapor pressures than other oils, because they have much higher molecular weights, e.g. about 2,000 to about 15,000, and therefore do not produce a significant amount of vapor.

Desirably, operation of a prosthetic knee in shear mode in one embodiment preferably utilizes a carrier fluid with a pour point (test method ASTM D-97) preferably ranging from about −70° C. to about −40° C., from about −65° C. to about −45° C., but also including about −50° C., −55° C., −60° C., and ranges encompassing these temperatures. ASTM D-97 method defines "pour point" as the lowest temperature at which movement of an oil is observed. In another embodiment, operation of a prosthetic knee in shear mode preferably utilizes a carrier fluid with a percent volatility at 121° C. (test method ASTM D-972) preferably ranging from about 0.01% to about 20%, from about 0.02% to about 15%, from about 0.03% to about 12%, but also including about 0.05%, 0.08%, 0.1%, 0.2%, 0.3%, 0.4%, 0.5%, 0.7%, 0.9%, 1%, 3%, 5%, 7%, 9%, 17%, and ranges encompassing these percentages.

More specifically, when used in combination with a prosthetic knee as previously disclosed, desirable MR fluids for use in certain embodiments comprise a carrier fluid and polarizable particles. More specifically, in one embodiment used in combination with a prosthetic knee, the MR fluid comprises one or more PFPE oil carrier fluids and polarizable particles. In one embodiment, the iron particles comprise from about 1 to about 60% (v/v) of the total MR fluid volume, preferably from about 10 to about 50% (v/v), more preferably from about 20 to about 40% (v/v), but also including about 5, 15, 25, 30, 35, 45, and 55% (v/v), and ranges encompassing these percentages.

Other ingredients can be optionally added to the carrier fluids of preferred embodiments to enhance the performance properties of preferred carrier fluids. In some embodiments, preferred additives include, but are not limited to, functionalized carrier fluids. In embodiments comprising perfluorinated polyethers, desirable additives can also include, but are not limited to, functionalized PFPE oils as well as derivatized fluoropolymers. Suitable candidates for mono-functionalized PFPE derivatives include, but are not limited to silane, phosphate, hydroxyl, carboxylic acid, alcohol and amine functions. Suitable candidates for difunctional PFPE derivatives include, but are not limited to, dihydroxyl, ethoxy ether, isocyanate, aromatic, ester and alcohol functions. In some embodiments, functionalized perfluorinated polyether fluid additive comprises one or more functional groups selected from the group consisting of silane, phosphate, hydroxyl, carboxylic acid, amine, dihydroxyl, ethoxy ether, isocyanate, aromatic, ester and alcohol functions. More specifically, in one embodiment comprising perfluorinated polyethers, a preferred functionalized PFPE oil comprises a poly(hexafluoropropylene epoxide) with a carboxylic acid located on the terminal fluoromethylene group. As presently contemplated preferred functionalized PFPE oils are Krytox(157 FSL and Krytox.RTM. 157 FSM available from E.I. du Pont de Nemours and Company, (Wilmington, Del., USA). In another embodiment, a preferred fluoropolymer comprises a parafluoropropene and oxygen polymerized amide derivative. As presently contemplated a preferred parafluoropropene and oxygen polymerized amide derivative additive is FOMBLIN DA 306 available from Solvay Solexis (Thorofare, N.J., USA).

The ingredients may be combined in any order and mixed by any suitable means including, but not limited to, stirring, agitation, blending or sonification. In accordance with a preferred embodiment, the MR fluid is prepared as described above. Prior to loading into the prosthetic knee, the MR fluid is stirred under vacuum using a high speed stirrer to remove any dissolved gases. In a preferred embodiment, the MR fluid is heated to about 90 to about 160° F., more preferably to about 100 to about 150° F., even more preferably to about 110 to about 130° F., but also including about 95, 105, 115, 120, 122, 125, 135, 140, 145, and 155° F., under vacuum prior to loading into the prosthetic knee.

In another preferred embodiment, the MR fluid is heated at ambient pressure prior to being placed under vacuum. While under vacuum, agitation or stirring of the MR fluid is preferred but not required. After the MR fluid is released from the vacuum, the MR fluid is loaded into the prosthetic knee. The loading of the prosthetic knee involves adding the MR fluid to the knee and then placing the knee under vacuum. While under vacuum the knee is optionally agitated. To reduce the vacuum pressure, an inert gas is added into the vacuum chamber. Once, the vacuum is fully released, the prosthetic knee is removed and closed. The vacuum fill process should be carefully monitored as exiting air may blow enough MR fluid out of the funnel to require fluid volume replenishment.

EXAMPLES

Example 1

MR Fluid Preparation

To prepare the MR fluid, the additives were mixed with the carrier fluids and stirred. Carrier fluid was added to the iron particles and the ingredients were stirred. A Branson Digital Sonifier, Model 450, was used to disperse the iron particles in the carrier fluid. The MR fluid was then placed on the sonifier table, with the probe adjusted so that the majority of the probe was immersed in the MR fluid without touching the bottom of the mixture jar. The MR fluid was then sonicated for 1.5 minutes at 50% intensity while the sonifier table rotated. The MR fluid was checked periodically to ensure that the mixture did not become too hot. A fan was used to cool the MR fluid. Once the cycle was complete, the jar was rotated to wash down any particles that were adhered to the walls of the jar. The sonification step was then repeated two more times. Once complete, the MR fluid was removed from the sonifier and a final stir of the MR Fluid was performed to ensure that there were no clumps in the MR fluid. The MR fluid was then placed in an oven for two hours at 50° C.(122° F.).

Example 2

Prosthetic Knee MR Fluid Loading

When the MR fluids as described herein are used in combination with a prosthetic knee, for example, a knee as described in U.S. Patent Publication No. 2001/0029400A1, certain characteristics of the fluid as well as the knee may be desired. In one embodiment, such as shown in FIGS. 4 and 5 of U.S. 2001/0029400A1 and FIGS. 1 and 2 disclosed herein and described in further detail below, a knee may contain a cavity or passage for holding MR fluid between a plurality of rotors and stators. The number of rotors and stators in certain embodiments may be increased or reduced in order to alter the off-state or low-end torque properties of the MR fluid used in combination with the knee. In one embodiment, the number of rotors and stators preferably range from about 50 to about 90, preferably from about 55 to about 70, but also including about 57, 59, 61, 63, 65, 67, and ranges encompassing these amounts. The knee cavity may contain a volume of about 1 to about 10 ml, preferably from about 2 to about 9 ml, more preferably from about 3 to about 8 ml, but also including about 4, 5, 6, and 7 ml. In one embodiment, the MR fluid fills the cavity to about 70% of its total volume, but may range from about 50 to about 100% as well about 55, 60, 65, 75, 80, 85, 90 and 90%. The MR fluid advantageously demonstrates one or more of the following: relatively low volatility, stable viscosity, thermal stability, and a stable composition. In addition, in certain embodiments it is desirable that the cavity or passage containing the MR fluid does not exhibit undesirable pressure levels. Without wishing to be bound by any theory, it is believed that an unsuitable fluid may release gases or volatilize causing pressure within the prosthetic knee to increase to an undesirable level. If the pressure is too high, the integrity of the prosthetic knee seals can be compromised. In certain embodiments it is desirable that a prosthetic knee utilizing a MR fluid produces torque of about 0.1 to about 200 Newton-meters, more preferably about 0.3 to about 150 Newton-meters, even more preferably about 0.5 to about 100 Newton-meters, but also including about 0.8, 1, 2, 3, 4, 5, 6, 7, 8, 9, 10, 20, 30, 40, 50, and 75 Newton-meters.

FIGS. 1 and 2 show a controllable rotary prosthetic knee joint 210 having features and advantages in accordance with one preferred embodiment of the present invention. The prosthetic knee 210 generates controllable dissipative forces preferably substantially along or about the knee axis of rotation 224.

The electronically controlled knee 210 generally comprises a generally central core 212 in mechanical communication with a pair of rotatable side plates 216, 218, an electromagnet 214, a plurality of blades or rotors 220 in mechanical communication with a rotatable inner spline 222, a plurality of blades or stators 230 in mechanical communication with a rotatable outer spline 232, a pair of ball bearings 226, 228 for transferring rotary motion to a pair of outer side walls or forks 236, 238. The rotation is substantially about the knee axis of rotation 224.

The plurality of rotors 220 and stators 230 are preferably interspersed in an alternating fashion and the gaps or micro-gaps between adjacent blades 220 and 230 comprise thin lubricating films of a magnetorheological (MR) fluid, which thereby resides in the cavity or passage formed between the inner spline 222 and the outer spline 232. This preferred embodiment provides a controllable and reliable artificial knee joint, which advantageously has a wide dynamic torque range, by shearing the MR fluid in the multiple gaps or flux interfaces between adjacent rotors 220 and stators 230.

Preferably, end-threaded rods 248 and nuts 250 are used to secure selected components of the prosthetic knee 210, thereby allowing a straightforward assembly and disassembly procedure with a minimum of fasteners. Alternatively, or in addition, various other types of fasteners, for example, screws, pins, locks, clamps and the like, may be efficaciously utilized, as required or desired, giving due consideration to the goals of providing secure attachment, and/or of achieving one or more of the benefits and advantages as taught or suggested herein.

Preferably, the core 212 and associated side plates 216, 218 are formed of a magnetically soft material of high flux saturation density and high magnetic permeability. Thus, when the electromagnet 214 is actuated a magnetic field, circuit or path is generated or created within the knee joint 210. In one preferred embodiment, the magnetic field passes longitudinally (parallel to the axis of rotation 224) through the central core 212, radially through the side plate 218, laterally (parallel to lateral direction 242) through the interspersed set of rotors 220 and stators 230 and the magnetorheological (MR) fluid, and radially through the side plate 216. The orientation or positioning of the electromagnet 214 and the direction of current flow through it determines the polarity of the magnetic field, and thereby determines whether the magnetic field passes radially inwards or outwards through the side plate 218, and hence in the correspondingly opposite direction through the side plate 216. The portion of the magnetic field passing through the core 212 and side plates 216, 218 generally defines the magnetic return path while the active or functional magnetic field is generally defined by the magnetic path through the rotors 220, stators 230 and MR fluid residing therebetween.

Figure 8:
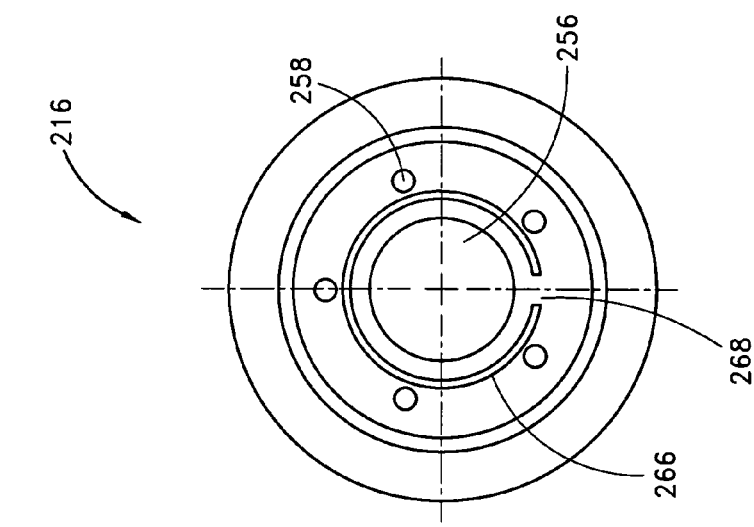
FIG. 8 is a rear view of the core side plate of FIG. 7.
Figure 9:
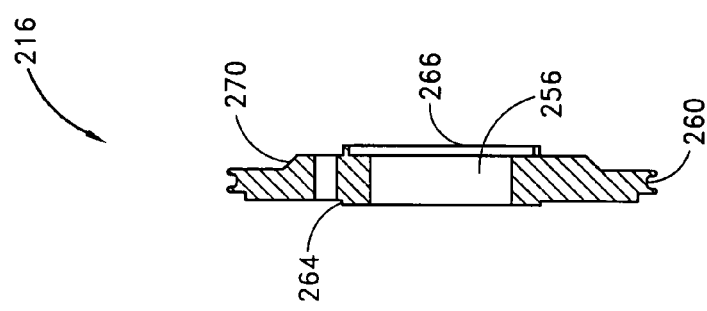
FIG. 9 is a cross section view along line 11—11 of FIG. 7.
Figure 7:
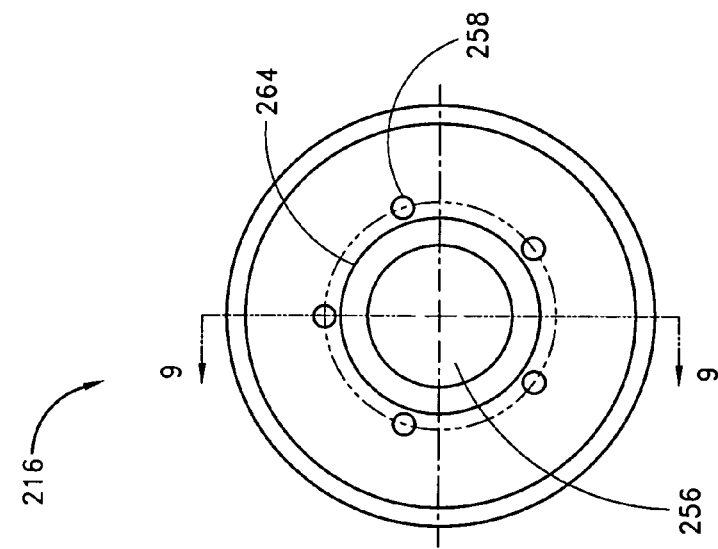
FIG. 7 is a front view of one of the core side plates of FIG. 1 having features and advantages in accordance with one preferred embodiment of the present invention.

FIGS 7–9 show one preferred embodiment of the core side plate or disk 216 of the prosthetic knee joint. 210. The core side plate 216 preferably comprises a circular groove 260 to receive an O-ring 262 (FIG. 1), lip seal or gasket and the like. This provides a dynamic seal between the rotatable side plate 216 and the inner surface of the rotatable outer spline 232 and prevents leakage of MR fluid from the knee 210. The other side plate 218 is similarly configured to receive an O-ring 262 (FIG. 1) and provide a dynamic seal. In an alternative preferred embodiment, two grooves or flanges are provided on the inner surface of the outer spline 232 to receive O-rings or the like and provide a dynamic seal between the core side plates 216, 218 and the outer spline 232.

The O-rings 262 are fabricated from a suitable rubber material or the like such as Viton, Teflon and Neoprene among others. In one preferred embodiment, the O-rings 262 have an inner diameter of about 50 mm and a width of about 1.5 mm. In other preferred embodiments, the dynamic seals can be dimensioned and/or configured in alternate manners with efficacy, as required or desired, giving due consideration to the goals of providing reliable seals, and/or of achieving one or more of the benefits and advantages as taught or suggested herein.

The inner surface of the core side plate 216 preferably has a generally circular shoulder or step 264 for aligning or locating with the inner spline 222 (FIG. 1). The outer surface of the core plate 216 preferably has a generally ring-shaped shoulder or step 266 for aligning or locating with the outer fork 236 (FIG. 1). Optionally, the step 266 may include a cut 268 to allow clearance space for electrical wires or leads. Other holes around the central cavity 256 may be provided for passage of electrical wires or leads. Preferably, the outer surface of the core side plate 216 includes a tapered portion 270. This advantageously decreases weight, saves material and also provides clearance space to facilitate assembly.

The core side plate 216 is preferably fabricated form a material having a high saturation flux density, a high magnetic permeability and low coercivity. Advantageously, this facilitates in the construction of an artificial knee or brake that is compact and light weight, and also strong. In one preferred embodiment, the core plate 216 comprises an integral unit. In another preferred embodiment, the core plate 216 is formed of laminated sheets to advantageously reduce or minimize eddy losses.

Preferably, the core plate 216 comprises an iron-cobalt (FeCo) high magnetic saturation alloy. In one preferred embodiment, the core plate 216 comprises Vacoflux 50 as available from Vacuumschmelze of Hanau, Germany. In another preferred embodiment, the core plate 216 comprises Iron-Cobalt High Saturation Alloy (ASTM A-801 Type 1 Alloy). In yet another preferred embodiment, the core plate 216 comprises Vacoflux 17 as available from Vacuumschmelze of Hanau, Germany. In a further preferred embodiment, the core plate 216 comprises Hiperco Alloy 50. In other preferred embodiments, the core plate 216 can be efficaciously fabricated from alternate soft magnetic materials or the like, as required or desired, giving due consideration to the goals of providing a suitably compact, light weight and/or durable prosthetic knee joint, and/or of achieving one or more of the benefits and advantages as taught or suggested herein.

In one preferred embodiment, the material comprising the core plate 216 has a saturation flux density of about 2.2 Tesla. Such a high saturation flux density is desirable because it allows a compact and light weight design. For example, if a material having a lower saturation flux density was utilized, the cross-sectional area of the return path through the core plate 216 in the direction of the applied magnetic field would have to be increased to achieve the same dynamic torque range. In other preferred embodiments, the core side plate saturation flux density can be higher or lower, as needed or desired, giving due consideration to the goals of providing a suitably compact, light weight and/or durable prosthetic knee joint, and/or of achieving one or more of the benefits and advantages as taught or suggested herein.

Preferably, the core side plate 216 is formed by machining followed by heat treatment in a hydrogen atmosphere to achieve optimal magnetic properties. In other preferred embodiments, the core side plate 216 can be efficaciously fabricated from other techniques, for example, casting, forging, molding, laminating, among others, as required or desired, giving due consideration to the goals of providing desired magnetic properties and a suitably compact, light weight and/or durable artificial knee, and/or of achieving one or more of the benefits and advantages as taught or suggested herein.

Figure 10:
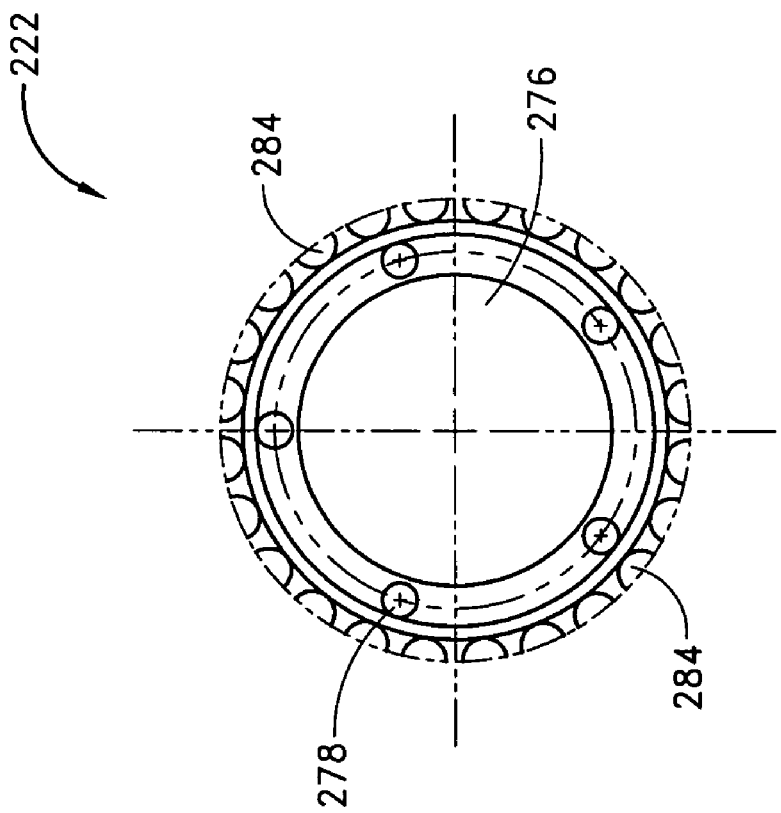
FIG. 10 is an end view of the inner spline of FIG. 1 having features and advantages in accordance with one preferred embodiment of the present invention.

FIG. 10 shows one preferred embodiment of the inner spline 222 of the prosthetic knee joint 210. The inner spline 222 is preferably generally cylindrical in shape and comprises a substantially central cylindrical cavity or through hole 276 for receiving the electromagnet or magnetic coil 214 (FIG. 1). Alternatively, other suitable shapes for the inner spline 222 and cavity 276 may be efficaciously utilized, as needed or desired.

Preferably, the inner spline 222 comprises a plurality of approximately equally spaced longitudinal through holes 278 arranged in a generally circular fashion to receive end-threaded rods or bolts and the like to secure selected components of the prosthetic knee 210, such as the core side plates 216, 218 and the inner spline 222. These holes 278 are generally aligned with corresponding holes 258 of the core side plates 216, 218.

In one preferred embodiment, the inner spline 222 comprises five holes 278. In another preferred embodiment, the inner spline 222 comprises three holes 278. Alternatively, fewer or more holes 278 arranged in other fashions may be provided, as needed or desired.

The inner spline 222 preferably comprises a circular groove 260 at each end to receive respective O-rings 282 (FIG. 1) or gaskets and the like. This provides a static seal between the inner spline 222 and the side plates 216, 218, since these components rotate together during knee rotation, and prevents leakage of MR fluid from the knee 210. In an alternative preferred embodiment, a respective groove or flange is provided on the inner surfaces of either or both plates 216, 218 to receive O-rings or the like and provide a static seal.

The O-rings 282 are fabricated from a suitable rubber material or the like such as Viton, Teflon and Neoprene among others. In one preferred embodiment, the O-rings 282 have an inner diameter of about 30.5 mm (1.201 inches) and a width of about 0.76 mm (0.030 inches). In other preferred embodiments, the static seals can be dimensioned and/or configured in alternate manners with efficacy, as required or desired, giving due consideration to the goals of providing reliable seals, and/or of achieving one or more of the benefits and advantages as taught or suggested herein.

The outer surface of the inner spline 222 preferably has a plurality of approximately equally spaced longitudinal grooves 284 which are adapted to engage corresponding teeth of the rotors 220. In one preferred embodiment, the grooves 284 are generally semi-circular in shape. In another preferred embodiment, the grooves 284 are generally rectangular or square shaped with rounded corners. In other preferred embodiments, the grooves 284 can be efficaciously shaped and/or configured in alternate manners, as required or desired, giving due consideration to the goals of providing reliable load transmission from the rotors 220 to the inner spline 222, and/or of achieving one or more of the benefits and advantages as taught or suggested herein.

The inner spline 222 is preferably fabricated from titanium or a titanium alloy, and more preferably from 16A1–14V titanium alloy. Advantageously, the use of titanium or titanium alloys provides a near zero magnetic permeability and a yet strong, hard surface with low weight to engage the rotors and transmit torque from them. An additional benefit is that the high resistivity of the material (titanium or titanium alloy) reduces energy losses due to induced eddy currents. In other preferred embodiments, the inner spline 222 can be efficaciously fabricated from other metals, alloys, plastics, ceramics among others, as required or desired, giving due consideration to the goals of providing an inner spline 222 of near zero magnetic permeability, and a suitably compact, light weight and/or durable artificial knee, and/or of achieving one or more of the benefits and advantages as taught or suggested herein.

Preferably, the inner spline 222 is formed by machining. In other preferred embodiments, the inner spline 222 can be efficaciously fabricated from other techniques, for example, casting, forging, molding, among others, as required or desired, giving due consideration to the goals of providing a suitably compact, light weight and/or durable artificial knee, and/or of achieving one or more of the benefits and advantages as taught or suggested herein.

In one preferred embodiment, the prosthetic knee 210 comprises an angle sensing potentiometer 322 (FIG. 1). The potentiometer 322 is connected to an arm 324 and a mounting plate 326. The mounting plate 326 is connected to the fork 238 utilizing screws 328 or the like and spacers 330. An end 332 of the arm 324 is mechanically connected to the angled outer surface 334 of the fork 238 utilizing suitable screws or the like.

In one preferred embodiment of the present invention, the prosthetic knee 210 further comprises an extension assist to help straighten the leg by urging or biasing the leg to extension by applying a controlled torque or force. Any one of a number of devices, such as a spring-loaded extension assist, as known in the art may be used in conjunction with the present invention.

The mounting forks 236, 238 (FIG. 1) of the magnetorheologically actuated prosthetic knee 210 are preferably in mechanical communication with the bearings 226, 228 respectively and transfer rotary motion to a pylon or artificial shin portion of the amputee. Threaded studs 306 or other suitable connectors or fasteners are used to facilitate connection of the mounting forks 236, 238 to a pylon or artificial shin portion of the amputee.

Preferably, the mounting forks 236, 238 are fabricated from anodized 7075-T6 aluminum alloy. In other preferred embodiments, the mounting forks 226, 238 can be efficaciously fabricated from other metals, alloys, plastics, ceramics among others, as required or desired, giving due consideration to the goals of providing suitably strong, durable, light weight and/or substantially non-magnetic mounting forks 226, 238, and/or of achieving one or more of the benefits and advantages as taught or suggested herein.

In one preferred embodiment, the mounting forks 236, 238 are formed by machining. In other preferred embodiments, the mounting forks 236, 238 can be efficaciously fabricated from other techniques, for example, casting, forging, molding, among others, as required or desired, giving due consideration to the goals of providing a suitably compact, light weight and/or durable artificial knee, and/or of achieving one or more of the benefits and advantages as taught or suggested herein.

In one preferred embodiment, and as shown in FIG. 1, the prosthetic knee 210 further comprises a flexion stop system or assembly comprising a cushioned stop or restraint assembly or system 246. The flexion stop system controls the maximum allowable flexion angle by physically limiting the rotation between the outer side forks 236, 238 and the outer spline 232, and hence the rotation of the knee joint. The stop system 246 (FIG. 1) generally comprises a plurality of stops, bands or strips 312, 314 and 316.

A measured volume of MR fluid was then transferred into a funnel inserted into the prosthetic knee actuator. The knee was placed in the vacuum chamber and the chamber was sealed with a bell jar. Vacuum was slowly drawn to 28" Hg. The knee was periodically agitated during this procedure.

The vacuum chamber was slowly filled with nitrogen gas to remove the vacuum. Vacuum was slowly released at about 2" Hg per 10 seconds. The knee was agitated to help force the fluid into the knee. Nitrogen was disconnected from the vacuum chamber when the gage read zero. The vacuum chamber was then unsealed and the knee was removed. The funnel was then removed from the knee. Care was taken so as to avoid tipping the knee during this process, which would have resulted in a release of the nitrogen head. The knee was closed by inserting the appropriate set screw with a torque of about 2.5 Nm applied to the screw.

Example 3

MR Fluid Settling Tests

Settling tests were conducted for thirteen different MR fluids. The rate of settling varied significantly and was found to be a function of iron particle size, the use of additives, and the viscosity of the fluids.

Procedure for Settling Tests

MR fluids were formulated by adding carrier oil, with or without an additive, to a jar containing a weighed aliquot of carbonyl iron particles. For formulations containing an additive, the additive was blended with the carrier oil prior to mixing with the iron particles. The components were mixed by hand for several minutes and then the iron particles were dispersed using high frequency ultrasonic energy supplied by a Branson Digital Sonifier, Model 450. The fluids were subjected to 2–3 cycles of ultrasonic energy, each cycle having a duration of 1.5 minutes and power amplitude of approximately 50%. The fluids were then mixed again by hand to insure complete dispersion of the iron particles. Fluids were not degassed prior to starting the settling tests.

Approximately 8 mL of each of the well-mixed MR fluids were transferred to 10 mL graduated cylinders. The cylinders were closed by placing a ground glass stopper into the neck of each cylinder.

The initial volume of MR fluid was recorded and the volume of settled material was read and recorded at regular intervals for a period of twenty-one days. The fraction of settling was defined as the volume of carrier oil, which separated from the MR fluid and floated on the top of the MR fluid divided by the initial fluid volume.

TABLE 1

MR Fluids Tested

| MR Fluid | BASF Particle Type | Particle Loading (% (v/v) of total MR fluid) | Fluid Component (% (v/v) of total MR fluid) | Carrier Fluid (% (v/v) of total fluid component) | Dupont 157 FSL Additive (% (v/v) of total fluid component) |
|---|---|---|---|---|---|
| HQ81FS-28 | HQ | 28% | 72% | 95% Nye 8130 | 5% |
| HQ85FSL-28 | HQ | 28% | 72% | 95% Nye 8510 | 5% |
| HS67FS5-32 | HS | 32% | 68% | 63.7% Nye 8510; 31.3% Dupont GPL-103 | 5% |
| HS8510FSL-25 | HS | 25% | 75% | 95% Nye 8510 | 5% |
| HS8510FSL-28H | HS | 28% | 72% | 95% Nye 8510 | 5% |
| HS85FS10-28 | HS | 28% | 72% | 90% Nye 8510 | 10% |
| HS85FS10-32 | HS | 32% | 68% | 90% Nye 8510 | 10% |
| HS85FS1-32 | HS | 32% | 68% | 99% Nye 8510 | 1% |
| HS85FS5-32 | HS | 32% | 68% | 95% Nye 8510 | 5% |
| OM8510-25 | OM | 25% | 75% | 100% Nye 8510 | None |
| OM85-25-1 | OM | 25% | 75% | 99% Nye 8510 | 1% |
| OMPF-25 | OM | 25% | 75% | 100% Nye 8130 | None |
| OMPFA-25 | OM | 25% | 75% | 95% Nye 8130 | 5% |

HQ Particle Size Ranges from about 0.5–2.0μ
HS Particle Size Ranges from about 1.5–3.5μ
OM Particle Size Ranges from about 2–9μ

Results

In general the largest iron particles, OM grade, settled the fastest, especially when the viscosity of the fluid was reduced by including the Dupont 157 FSL additive in the formulation. However, the settling curves for the larger OM grade particles were initially steep and then leveled off after 10 to 14 days. Settling rates for the smaller iron particles, HS and HQ grade, were nearly linear over the twenty-one day test period.

Overall, MR fluids with lower settling rates demonstrated longer life and greater durability during subsequent bench testing in prosthetic knees. MR fluids with high settling rates produced hard caked settled iron particles. These fluids performed poorly in subsequent bench testing in prosthetic knees. MR fluids with low settling rates produce soft settled iron particles. These fluids generally performed well in subsequent prosthetic knee bench tests.

Example 4

Viscosity and Shear Rate Testing

Dynamic viscosity of three mixed carrier oils and six MR fluids made from the mixed carrier oils were measured as a function of shear rate. Viscosity measurements were performed at ambient temperature (22° C.) using a Rheometric Scientific (TA Instruments) RFS-II rheometer with a parallel plate sample cell. All samples were run in duplicate with approximately 1cc of sample. Five of the samples were rerun in duplicate on a second day due to incomplete mixing of the first samples.

Samples of mixed carrier fluids as well as MR fluids containing mixed carrier fluids were tested. The samples and viscosity measurements were as follows:

TABLE 2

| Sample Name | Fluid Component %((v/v)) | BASF HS particles %((v/v)) | Viscosity (cP) at 100 s$^{-1}$ |
|---|---|---|---|
| A | 100[1] | 0% | 115 |
| B | 100[2] | 0% | 121 |
| C | 100[3] | 0% | 145 |
| A-32 | 68[1] | 32% | 681 |

TABLE 2-continued

| Sample Name | Fluid Component %((v/v)) | BASF HS particles %((v/v)) | Viscosity (cP) at 100 s$^{-1}$ |
|---|---|---|---|
| A-40 | 60[1] | 40% | 1371 |
| B-32 | 68[2] | 32% | 780 |
| B-40 | 60[2] | 40% | 1651 |
| C-32 | 68[3] | 32% | 917 |
| C-40 | 60[3] | 40% | 1725 |

[1]Fluid component consisting of 47.5% (v/v) Nye 8510 carrier fluid, 47.5% (v/v) Dupont GPL-103 carrier fluid; 5% (v/v) Dupont 157-FSL additive.
[2]Fluid component consisting of 63.7% (v/v) Nye 8510 carrier fluid, 31.3% (v/v) Dupont GPL-103 carrier fluid; 5% (v/v) Dupont 157-FSL additive.
[3]Fluid component consisting of 71.3% (v/v) Nye 8510 carrier fluid, 23.7% (v/v) Dupont GPL-103 carrier fluid; 5% (v/v) Dupont 157-FSL additive.

Figure 3:
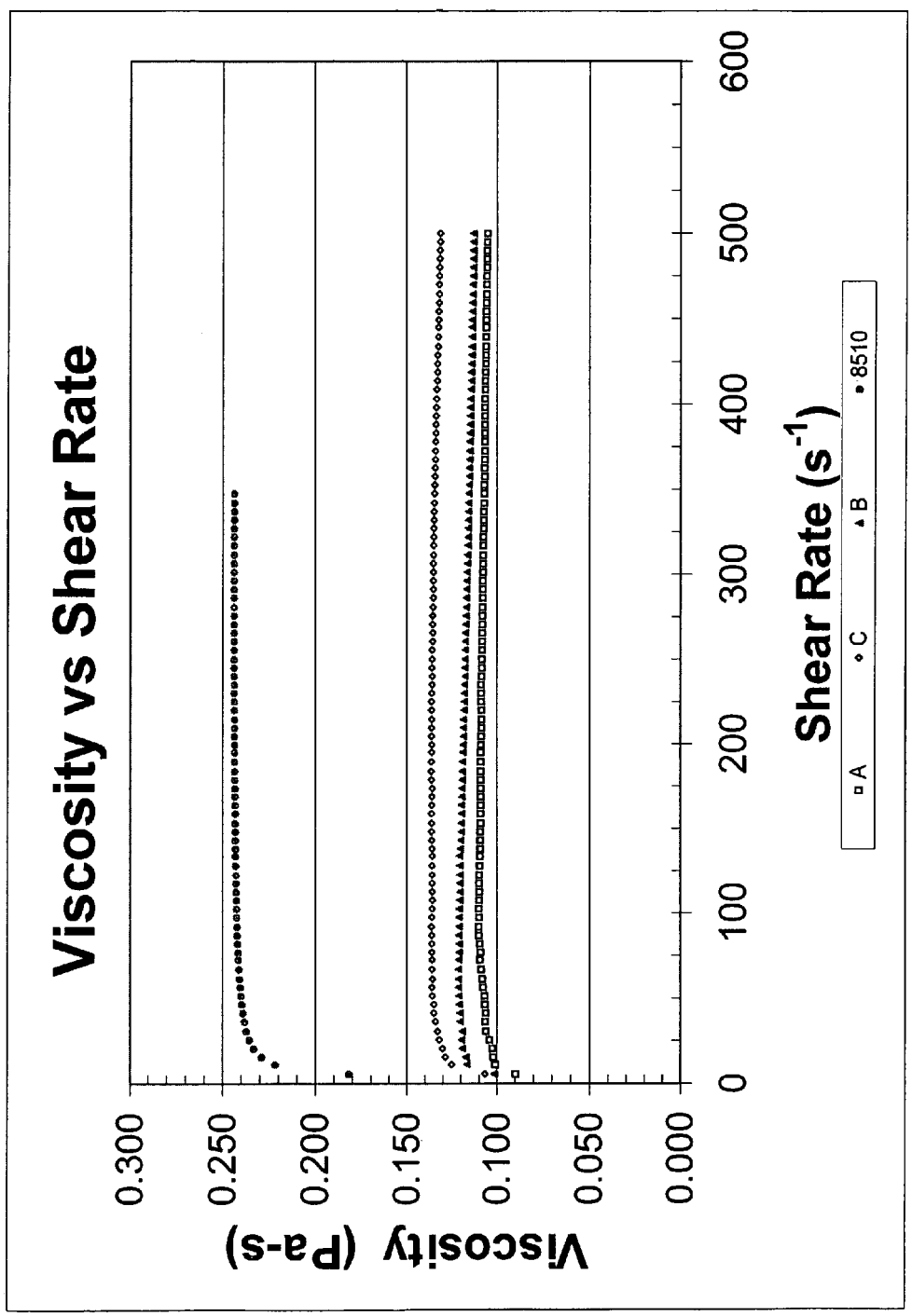
FIGS. 3–5 illustrate dynamic viscosity curves for various carrier oils and MR fluid samples.

The dynamic viscosity curves which were measured at ambient temperature (22° C.), for the samples above are illustrated in FIGS. 3, 4, and 5. FIG. 3 represents the viscosity, η, versus shear rate cures for the three mixed carrier oils, A–C, and a sample of 100% ((v/v)) Nye 8510 oil. All of the mixed carrier had a lower viscosity then Nye 8510. The typical viscosity specification value for Nye 8510 oil iss 65 cSt at 40° C., while the Dupont GPL-103 oil had a viscosity of 30 cSt at 40° C.

FIG. 4 represents the viscosity, η, versus shear rate curves for the three mixed carrier oil MR fluids containing 32% ((v/v)) of HS iron particles and a MR fluid which contains 100% Nye 8510 carrier oil and 32% ((v/v)) of HS iron. Viscosities of the mixed carrier oil MR fluids were less than the MR fluid containing only Nye 8510. This data demonstrated that it was possible to reduce the viscosity of a MR fluid by decreasing the viscosity of the carrier oil. Viscosity of the mixed carrier oil MR fluids was lowered in proportion to the amount of GPL-103, which was added to the carrier oil. The three mixed MR fluids exhibited Non-Newtonian behavior as the viscosity of these fluids changed continually with shear rate. The viscosity of these fluids was approximately six times that of the corresponding carrier oil at a shear rate of 100 $s^{-1}$.

FIG. 5 represents the viscosity, η, versus shear rate curves for the three mixed carrier oil MR fluids which contain 40% ((v/v)) of HS iron particles. The viscosities of these fluids were considerably larger than the viscosities of the MR fluids, which contained 32% ((v/v)) iron. Viscosity of the mixed carrier oil MR fluids containing 40% ((v/v)) iron was lower for the fluids with higher amounts of GPL-103, however, the viscosity curve for B-40 was higher than expected. This apparent anomaly was mostly likely caused by incomplete mixing of the viscous 40% ((v/v)) iron MR fluids prior to the viscosity measurements. The three MR fluids exhibited Non-Newtonian behavior as the viscosity of these fluids changed continually with shear rate. The viscosity of these fluids was approximately twelve times that of the corresponding carrier oil at a shear rate of 100 $s^{-1}$.

Figure 6:
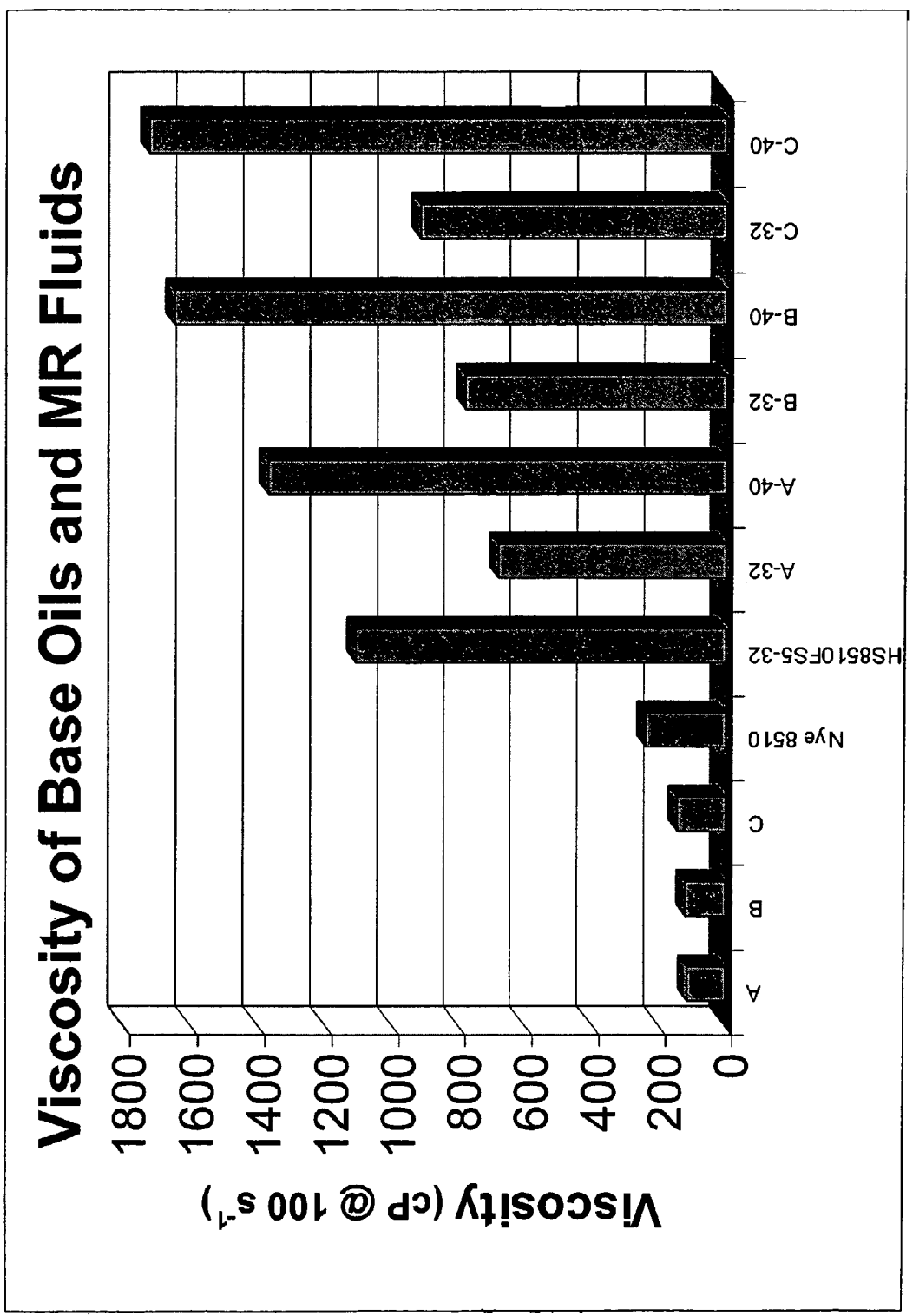
FIG. 6 illustrates a comparison of the viscosities of various carrier oils and MR fluids.

FIG. 6 summarizes the comparison of the viscosities of the three mixed carrier oils to Nye 8510 and the viscosities of the six mixed carrier oil MR fluids to that of a MR fluid containing only Nye 8510. Nye 8510 had a viscosity of 240 cP at 100 $s^{-1}$, while the three mixed carrier oils were well below 200 cP. The MR fluid which contained only Nye 8510 and 32% ((v/v)) iron, namely HS8510FS5-32, has a viscosity of 1,100 cP at 100 $s^{31\ 1}$, while the MR fluids containing mixed carrier oils and 32% ((v/v)) iron had viscosities of 680, 780 and 917 cP at 100 $s^{-1}$ respectively, for the fluids which contain 50, 67 and 75% ((v/v)) of Nye 8510. Viscosity of the MR fluids containing 32% ((v/v)) iron increased with increasing amounts of the more viscous Nye 8510. Viscosity of the MR fluids containing 40% ((v/v)) iron also increased with increasing amounts of Nye 8510.

Results indicated that the three carrier oils exhibited near Newtonian behavior, while the six MR fluids all exhibited Non-Newtonian behavior. Viscosity of the MR fluids were shown to be a function of both iron loading and carrier oil viscosity. For MR fluids with 32% ((v/v)) iron loading the viscosity was approximately six times that of the corresponding carrier fluid. For MR fluids with 40% ((v/v)) iron loading the viscosity was about twelve times that of the corresponding carrier fluid. All of the MR fluids exhibited thinning i.e. a reduction in viscosity as a function of shear rate, especially at low shear rates.

Example 5

Prosthetic Knee Testing

Numerous prosthetics knees operating in shear mode were filled with various MR fluids and tested for fluid performance, low-end torque, cavity pressure, and overall durability of the knee. Testing was performed to simulate use of the knee by an amputee. The knees were tested using a custom made test bench in conjunction with LabVIEW data acquisition software (National Instruments). The test machine rotated the prosthetic knees at a rate of 32,000 cycles per day in order to simulate accelerated knee usage. Prosthetic knees of varying configurations were used with numerous MR fluid compositions. The goal was to achieve three million cycles without knee failure. Due to limited equipment, testing of several knees was cut short in order to test other fluids and/or knee configurations. The following table illustrates some of the testing.

TABLE 3

| Fluid Name | Fluid Composition* | Fluid Performance | Duration of Test |
| --- | --- | --- | --- |
| OMPF-25 | 75% fluid component[1]; 25% BASF OM particles. | Unit ran smoothly, off state torque at end of test was 0.7 N-m. Applied field torque at end was 49 N-m. | 2.2 million cycles |
| HS8510FSL-28 | 72% fluid component[2]; 28% BASF HS particles. | Unit ran well, off state torque at end of test was 0.8 N-m. Applied field torque at end was 33 N-m. | 1.2 million cycles |
| HQ8510FSL-28 | 72% fluid component[2]; 28% BASF HQ particles. | Unit ran well, off state torque at 2.2 million cycles was 0.8 N-m. Applied field torque at 2.2 million cycles was 43 N-m. | 2.4 million cycles |
| HS8510FSL-25 | 75% fluid component[2]; 25% BASF HS particles. | Unit ran well, off state torque at 800,000 cycles was 0.6 N-m. Applied field torque at 800,000 cycles was 40 N-m. | 862,000 cycles |
| HS67FSL-32 | 68% fluid component[3]; 32% BASF HS particles. | Two units, A1 and A2, produce improved initial applied field torque 47–50 N-m. Initial off state torque was in the range of 0.6–0.8 N-m. A1 at 433K was at 44 N-m. A2 at 290K was at 47 N-m. | A1 - 433K cycles. A2 - 290K cycles. |

*All percentages are % (v/v).
[1]Fluid component consisting of 100% Nye 8130 carrier fluid.
[2]Fluid component consisting of 95% Nye 8510 carrier fluid and 5% Dupont 157-FSL additive.
[3]Fluid component consisting of 63.7% Nye 8510 carrier fluid, 31.3% Dupont GPL-103 carrier fluid, and 5% Dupont 157-FSL additive.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the composition may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A magnetorheological fluid comprising polarizable particles and a fluid component,
   wherein the fluid component comprises a carrier fluid and an additive;
   wherein the additive comprises a parafluoropropene and oxygen polymerized amide derivative.

2. The magnetorheological fluid of claim 1 wherein the polarizable particles comprise iron particles.

3. The magnetorheological fluid of claim 2 wherein the iron particles range in size from about 0.2 to about 50 microns.

4. The magnetorheological fluid of claim 3 wherein the iron particles range in size from about 0.4 to about 10 microns.

5. The magnetorheological fluid of claim 4 wherein the iron particles range in size from about 0.5 to about 9 microns.

6. The magnetorheological fluid of claim 2 wherein the iron particles comprise about 1 to about 60% (v/v) of the total magnetorheological fluid volume.

7. The magnetorheological fluid of claim 6 wherein the iron particles comprise about 10 to about 50% (v/v) of the total magnetorheological fluid volume.

8. The magnetorheological fluid of claim 7 wherein the iron particles comprise more preferably from about 20 to about 40% (v/v) of the total magnetorheological fluid volume.

9. The maguetorheological fluid of claim 1 wherein the carrier fluid is selected from the group consisting of silicone, hydrocarbon, esters, ethers, fluorinated esters, fluorinated ethers, mineral oil, unsaturated hydrocarbons, and combinations thereof.

10. The magnetorheological fluid of claim 9 wherein the carrier fluid comprises one or more perfluorinated polyethers.

11. The magnetorheological fluid of claim 1 wherein the additive comprises from about 0.1 to about 20% (v/v) of the fluid component.

12. The magnetorheological fluid of claim 11 wherein the additive comprises from about 1 to about 15% (v/v) of the fluid component.

13. The magnetorheological fluid of claim 12 wherein the additive comprises from about 2 to about 10% (v/v) of the fluid component.

14. The magnetorheological fluid of claim 1 comprising:
    about 28% (v/v) iron particles; and
    about 72% (v/v) fluid component;
    wherein said fluid component comprises about 5% (v/v) additive and about 95% (v/v) perfluorinated polyether carrier fluid.

15. The magnetorheological fluid of claim 1 wherein the magnetorheological fluid is operable over a temperature range from about 10 to about 115° F.

16. The magnetorheological fluid of claim 1 wherein the carrier fluid has a viscosity at 104° F. of about 10 to about 100 cSt.

17. The magnetorheological fluid of claim 16 wherein the carrier fluid has a viscosity at 104° F. of about 30 to about 80 cSt.

18. The magnetorheological fluid of claim 17 wherein the carrier fluid has a viscosity at 104° F. of about 50 to about 70 cSt.

19. The magnetorheological fluid of claim 1 wherein the carrier fluid has a viscosity index from about 100 to about 340 based on kinematic viscosity at 104 and 212° F.

20. The magnetorheological fluid of claim 19 wherein the carrier fluid has a viscosity index from about 120 to about 320 based on kinematic viscosity at 104 and 212° F.

21. The magnetorheological fluid of claim 1 wherein the carrier fluid has a pour point ranging from about −70° C. to about −40° C.

22. The magnetorheological fluid of claim 1 wherein the carrier fluid ham a percent volatility at 121° C. ranging from about 0.01% to about 20%.

23. A magnetorheological fluid consisting of polarizable particles and a fluid component,
    wherein the fluid component consists essentially of a carrier fluid and an additive;
    wherein the carrier fluid consists essentially of one of the group consisting of silicone, hydrocarbon, esters, ethers, fluorinated esters, fluorinated ethers, mineral oil, and unsaturated hydrocarbons; and
    wherein the additive consists essentially of a functionalized perfluorinated polyether fluid.

24. A magnetorheological fluid comprising polarizable particles and a fluid component
    wherein the fluid component consists essentially of a carrier fluid and an additive;
    wherein the carrier fluid consists essentially of one of the group consisting of silicone, hydrocarbon, esters, ethers, fluorinated esters, fluorinated ethers, mineral oil, and unsaturated hydrocarbons; and
    wherein the additive consists essentially of a functionalized perfluorinated polyether fluid
    wherein the functionalized perfluorinated polyether fluid additive comprises a poly(hexafluoropropylene epoxide) with a carboxylic acid located on the terminal fluoromethylene group.

25. The magnetorheological fluid of claim 24 wherein the polarizable particles comprise iron particles.

26. The magnetorheological fluid of claim 25 wherein the iron particles range in size from about 0.2 to about 50 microns.

27. The magnetorheological fluid of claim 25 wherein the iron particles range in size from about 0.4 to about 10 microns.

28. The magnetorheological fluid of claim 25 wherein the iron particles range in size from about 0.5 to about 9 microns.

29. The magnetorheological fluid of claim 25 wherein the iron particles comprise about 1 to about 60% (v/v) of the total magnetorheological fluid volume.

30. The magnetorheological fluid of claim 29 wherein the iron particles comprise about 10 to about 50% (v/v) of the total magnetorheological fluid volume.

31. The magnetorheological fluid of claim 30 wherein the iron particles comprise more preferably from about 20 to about 40% (v/v) of the total magnetorheological fluid volume.

32. The magnetorheological fluid of claim 24 wherein the carrier fluid comprises one or more perfluorinated polyethers.

33. The magnetorheological fluid of claim 24 wherein the functionalized perfluorinated polyether fluid additive comprises one or more functional groups selected from the group consisting of silane, phosphate, hydroxyl, carboxylic acid, amine, dihydroxyl, ethoxy ether, isocyanate, aromatic, ester and alcohol functions.

34. The magnetorheological fluid of claim 24 wherein the additive comprises from about 0.1 to about 20% (v/v) of the fluid component.

35. The magnetorheological fluid of claim 34 wherein the additive comprises from about 1 to about 15% (v/v) of the fluid component.

36. The magnetorheological fluid of claim 35 wherein the additive comprises from about 2 to about 10% (v/v) of the fluid component.

37. A magnetorheological fluid comprising:
   about 32% (v/v) polarizable iron particles; and
   about 68% (v/v) fluid component;
   wherein said fluid component consists essentially of about 5% (v/v) additive and about 95% (v/v) perfluorinated polyether carrier fluid;
   wherein said additive consists essentially of poly(hexafluoropropylene epoxide) with a carboxylic acid located on the terminal fluoromethylene group.

38. The magnetorheological fluid of claim 37 wherein the iron particles range in size from about 0.2 to about 50 microns.

39. The magnetorheological fluid of claim 37 wherein the iron particles range in size from about 0.4 to about 10 microns.

40. The magnetorheological fluid of claim 37 wherein the iron particles range in size from about 0.5 to about 9 microns.

41. A magnetorheological fluid comprising polarizable particles and a fluid component,
   wherein the fluid component comprises a carrier fluid and an additive;
   wherein the additive comprises poly(hexafluoropropylene epoxide) with a carboxylic acid located on the terminal fluoromethylene group.

42. The magnetorheological fluid of claim 41 wherein the polarizable particles comprise iron particles.

43. The magnetorheological fluid of claim 42 wherein the iron particles range in size from about 0.2 to about 50 microns.

44. The magnetorheological fluid of claim 42 wherein the iron particles range in size from about 0.4 to about 10 microns.

45. The magnetorheological fluid of claim 42 wherein the iron particles range in size from about 0.5 to about 9 microns.

46. The magnetorheological fluid of claim 42 wherein the iron particles comprise about 1 to about 60% (v/v) of the total magnetorheological fluid volume.

47. The magnetorheological fluid of claim 46 wherein the iron particles comprise about 10 to about 50% (v/v) of the total magnetorheological fluid volume.

48. The magnetorheological fluid of claim 47 wherein the iron particles comprise more preferably from about 20 to about 40% (v/v) of the total magnetorheological fluid volume.

49. The magnetorheological fluid of claim 41 wherein the carrier fluid is selected from the group consisting of silicone, hydrocarbon, esters, ethers, fluorinated esters, fluorinated ethers, mineral oil, unsaturated hydrocarbons, and combinations thereof.

50. The magnetorheological fluid of claim 49 wherein the carrier fluid comprises one or more perfluorinated polyethers.

51. The magnetorheological fluid of claim 41 wherein the additive comprises from about 0.1 to about 20% (v/v) of the fluid component.

52. The magnetorheological fluid of claim 51 wherein the additive comprises from about 1 to about 15% (v/v) of the fluid component.

53. The magnetorheological fluid of claim 52 wherein the additive comprises from about 2 to about 10% (v/v) of the fluid component.

54. The magnetorheological fluid of claim 41 comprising:
   about 32% (v/v) iron particles; and
   about 68% (v/v) fluid component;
   wherein said fluid component comprises about 5% (v/v) additive and about 95% (v/v) perfluorinated polyether carrier fluid.

* * * * *

UNITED STATES PATENT AND TRADEMARK OFFICE
CERTIFICATE OF CORRECTION

| | | |
|---|---|---|
| PATENT NO. | : 7,101,487 B2 | Page 1 of 2 |
| APPLICATION NO. | : 10/722313 | |
| DATED | : September 5, 2006 | |
| INVENTOR(S) | : Henry Hsu et al. | |

It is certified that error appears in the above-identified patent and that said Letters Patent is hereby corrected as shown below:

In column 2, line 19, delete the word "parafluoropropene" and insert the word --perfluoropropene-- in its place.

In column 2, line 51, delete the word "parafluoropropene" and insert the word --perfluoropropene- in its place.

In column 2, line 56, delete the word "parafluoropropene" and insert the word --perfluoropropene-- in its place.

In column 3, line 66, delete the word "parafluoropropene" and insert the word --perfluoropropene-- in its place.

In column 5, line 1, delete the word "parafluoropropene" and insert the word --perfluoropropene-- in its place.

In column 5, line 6, delete the word "parafluoropropene" and insert the word --perfluoropropene-- in its place.

In column 7, line 66, delete the word "parafluoropropene" and insert the word --perfluoropropene-- in its place.

In column 8, line 1, delete the word "parafluoropropene" and insert the word --perfluoropropene-- in its place.

In column 8, line 46, delete the word "parafluoropropene" and insert the word --perfluoropropene-- in its place.

UNITED STATES PATENT AND TRADEMARK OFFICE
CERTIFICATE OF CORRECTION

PATENT NO. : 7,101,487 B2
APPLICATION NO. : 10/722313
DATED : September 5, 2006
INVENTOR(S) : Henry Hsu et al.

It is certified that error appears in the above-identified patent and that said Letters Patent is hereby corrected as shown below:

In column 8, line 51, delete the word "parafluoropropene" and insert the word --perfluoropropene-- in its place.

In column 11, line 12, delete the word "parafluoropropene" and insert the word --perfluoropropene-- in its place.

In column 11, line 14, delete the word "parafluoropropene" and insert the word --perfluoropropene-- in its place.

In column 21, line 34, Claim 1, delete the word "parafluoropropene" and insert the word --perfluoropropene-- in its place.

Signed and Sealed this

Twentieth Day of March, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,101,487 B2 |
| APPLICATION NO. | : 10/722313 |
| DATED | : September 5, 2006 |
| INVENTOR(S) | : Henry Hsu et al. |

It is certified that error appears in the above-identified patent and that said Letters Patent is hereby corrected as shown below:

At column 7, line 56, please delete "dihydioxyl" and insert -- dihydroxyl --, therefor.

At column 7, line 58, before "More" please insert -- In some embodiments, functionalized perfluorinated polyether fluid additive comprises one or more functional groups selected from the group consisting of silane, phosphate, hydroxyl, carboxylic acid, amine, dihydroxyl, ethoxy ether, isocyanate, aromatic, ester and alcohol functions. --

At column 10, line 53 through column 11, line 17, please delete the paragraph beginning "Other ingredients can be optionally added . . ." and ending "available from Solvay Solexis (Thorofare, N.J., USA)," and insert the following paragraph therefor:

-- In another embodiment, the MR fluid used in combination with a prosthetic knee may optionally comprise an additive. Suitable additives include, but are not limited to, functionalized carrier fluids as well as fluoropolymers. In one embodiment, the iron particles comprise from about 1 to about 60 % (v/v) of the total MR fluid volume, preferably from about 10 to about 50% (v/v), more preferably from about 20 to about 40% (v/v), but also including about 5, 15, 25, 30, 35, 45, and 55 % (v/v), and ranges encompassing these amounts. In one embodiment, the additive comprises from about 0.1 to about 20 % (v/v) of the carrier fluid, preferably from about 1 to about 15 % (v/v), more preferably from about 2 to about 10 % (v/v), but also including 2.5, 3, 3.5, 4, 4.5, 5, 5.5, 6, 6.5, 7, 7.5, 8, 8.5, 9, 9.5, 11, 12, 13, 14, 16, 17, 18, and 19 % (v/v). For

UNITED STATES PATENT AND TRADEMARK OFFICE
CERTIFICATE OF CORRECTION

| | |
|---|---|
| PATENT NO. | : 7,101,487 B2 |
| APPLICATION NO. | : 10/722313 |
| DATED | : September 5, 2006 |
| INVENTOR(S) | : Henry Hsu et al. |

It is certified that error appears in the above-identified patent and that said Letters Patent is hereby corrected as shown below:

example, in one embodiment a preferred MR fluid used in combination with a prosthetic knee in shear mode comprises about 32% (v/v) particles and about 68% (v/v) fluid component wherein said fluid component comprises about 5% (v/v) a perfluoropropene and oxygen polymerized amide derivative additive and about 95% (v/v) perfluorinated polyether carrier fluid. In another embodiment a preferred MR fluid used in combination with a prosthetic knee in shear mode comprises about 28% (v/v) particles and about 72% (v/v) fluid component wherein, said fluid component comprises about 5% (v/v) a perfluoropropene and oxygen polymerized amide derivative additive and about 95% (v/v) perfluorinated polyether carrier fluid. In another embodiment, a preferred MR fluid used in combination with a prosthetic knee in shear mode comprises about 32% (v/v) particles, and about 68% (v/v) fluid component wherein said fluid component comprises about 5% (v/v) poly(hexafluoropropylene epoxide) with a carboxylic acid located on the terminal fluoromethylene group additive and about 95% (v/v) PFPE oil carrier fluid. In another embodiment, a preferred MR fluid used in combination with a prosthetic knee in shear mode comprises about 28% (v/v) particles, and about 72 % (v/v) fluid component wherein said fluid component composes about 5% (v/v) poly(hexafluoropropylene epoxide) with a carboxylic acid located on the terminal fluoromethylene group additive and

UNITED STATES PATENT AND TRADEMARK OFFICE
CERTIFICATE OF CORRECTION

PATENT NO. : 7,101,487 B2
APPLICATION NO. : 10/722313
DATED : September 5, 2006
INVENTOR(S) : Henry Hsu et al.

It is certified that error appears in the above-identified patent and that said Letters Patent is hereby corrected as shown below:

about 95% (v/v) PFPE oil carrier fluid. In embodiments containing PFPE oil, the PFPE oil may comprise substantially all one PFPE oil or a mixture of one or more PFPE oils. --

Signed and Sealed this

Twenty-sixth Day of August, 2008

JON W. DUDAS
*Director of the United States Patent and Trademark Office*